US006488832B2

(12) United States Patent
Heller

(10) Patent No.: US 6,488,832 B2
(45) Date of Patent: Dec. 3, 2002

(54) ARRAY BASED ELECTROPHORETIC SYSTEM FOR THE ANALYSIS OF MULTIPLE BIOLOGICAL SAMPLES

(75) Inventor: Michael J. Heller, Encinitas, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/373,925

(22) Filed: Aug. 12, 1999

(65) Prior Publication Data
US 2002/0029967 A1 Mar. 14, 2002

Related U.S. Application Data

(63) Continuation of application No. 08/234,637, filed on Apr. 28, 1994, now Pat. No. 6,013,166, which is a continuation of application No. 07/698,482, filed on May 9, 1991, now abandoned.

(51) Int. Cl.$^7$ ................. G01N 27/26; G01N 27/447
(52) U.S. Cl. ................. 204/603; 204/452; 204/461; 204/612
(58) Field of Search ................. 204/452, 603, 204/612, 461

(56) References Cited

U.S. PATENT DOCUMENTS

| | | | | |
|---|---|---|---|---|
| 3,964,992 A | * | 6/1976 | Krotz | 204/616 X |
| 4,244,803 A | | 1/1981 | Aladjem et al. | 422/82.01 |
| 4,473,452 A | | 9/1984 | Cantor et al. | 204/458 |
| 4,702,814 A | | 10/1987 | Audeh | 204/616 |
| 4,737,251 A | | 4/1988 | Carle | 204/458 |
| 4,810,348 A | * | 3/1989 | Sarrine et al. | 204/612 X |
| 4,830,830 A | | 5/1989 | Tamotu et al. | 204/603 |
| 4,874,492 A | * | 10/1989 | MacKay | 204/612 X |
| 4,874,494 A | * | 10/1989 | MacKay | 204/612 X |
| 4,898,658 A | | 2/1990 | Karger et al. | 204/603 |
| 4,908,112 A | * | 3/1990 | Pace | 204/601 X |
| 4,997,537 A | | 3/1991 | Karger et al. | 204/453 |
| 5,062,942 A | * | 11/1991 | Kambara et al. | 204/616 |
| 5,091,652 A | | 2/1992 | Mathies et al. | 250/458 |
| 5,122,248 A | | 6/1992 | Karger et al. | 204/453 |
| 5,126,022 A | * | 6/1992 | Soane et al. | 204/458 |
| 5,162,654 A | * | 11/1992 | Kostichkact et al. | 204/612 X |

FOREIGN PATENT DOCUMENTS

JP          3-61853      *   3/1991

OTHER PUBLICATIONS

Nicholas N. Rampino et al, "Apparatus for Gel Electrophoresis with Continuous Monitoring of Individual DNA Molecules by Video Epifluorescence Microscopy" Analytical Biochemistry, vol. 194, No. 2, pp. 278–283, May 1, 1991.*

Andrews. *Electrophoresis: Theory, Techniques & Biochemical & Clinical Applications.* 2$^{nd}$Ed. (Oxford Univ Press), 7–8, 93–116, 153–164, 329–331, 1986.

(List continued on next page.)

Primary Examiner—Jill Warden
(74) Attorney, Agent, or Firm—Lyon & Lyon LLP

(57) ABSTRACT

The present invention relates to an electrophoretic method to effect differential net migration, the extent of said migration being dependent on molecular size, of electrically charged macromolecules through a gel support in a single dimension, which method comprises subjecting electrically charged macromolecules applied to a gel support to an electric field oriented along a single axis within the gel for a time period sufficient to effect migration in the direction of the oriented field and form a separation pattern in order of the respective molecular weights of the macromolecules in a distance of about 0.5 to about 20 millimeters, said gel support comprising about 3 to about 40 percent acrylamide, said electric field being applied in an amount of about 5 to about 100 volts per millimeter of gel support along the axis length, and said gel support having a width perpendicular to said axis of about 0.1 to 1.5 millimeters.

35 Claims, 7 Drawing Sheets

OTHER PUBLICATIONS

Campbell et al. "Electrophoresis Of Small Proteins In Highly Concentrated & Crosslinked Polyacrylamic Gradient Gels". *Anal. Biochem.*, 129, 31–36, 1983.

Compton et al. "Capillary Electrophoresis". *BioTechniques*, 6, (5), 432–440, Jan. 1988.

Drossman et al. "High Speed Separations Of DNA Sequencing Reactions By Capillary Electrophoresis". *Anal. Chem.*, 62, (9), 900–903, May 1, 1990.

Guttman et al. "Analytical & Micropreparative Ultrahigh Resolution Of Oligonucleotide by Polyacrylamide Gel High–Performance Capillary Electrophoresis". *Anal Chem.* 62, (2), 137–141, Jan. 15, 1990.

Jeppesen. "A Method For Separating DNA Fragments By Electrophoresis In Polyacrylamide Concentration Gradient Slab Gels". *Anal Biochem.*, 58, 195–207, 1974.

Jorgenson, Lukacs. "Capillary Zone Electrophoresis". *Science*, 222, 266–272, Oct. 21, 1983.

Lambert et al. "Microelectrophoretic Technique For Fractionation Of RNA". *Nature*, 215, 292–293, Apr. 20, 1968.

Lambert et al. "Extraction & Fractionation Of Low Molecular Weight RNA In The Microscale". *Nature*, 220, 1036–1037, Dec. 7, 1968.

Lambert et al. "Agarose Acylamide Composite Gels For Microfabrication Of RNA". *Nature*, 220, 1037–1039, Dec. 7, 1968.

Luckey et al. "High Speed DNA Sequencing By Capillary Electrophoresis". *Nucleic Acids Res.*, 18, (15), 4417–4421, Aug. 11, 1990.

Manwell. "A Simplified Electrophoretic System For Determining Molecular Weights Of Proteins". *Biochem J.*, 165, 487–495, 1977.

Matioli et al. "Electrophoresis Of Hemoglobin In Single Erythrocytes". *Science*, 150, 1824–1826, 1965.

Neuhoff et al. "Micro–analysis Of Pure Deoxyribonucleic Acid–Dependent Ribonucleic Acid Polymerase From *Escherichia coli*". *Biochem.J.*, 117, 623–631, 1970.

Orban et al. "Sieving Of Ionic Constituents Across Moving Boundaries In Gel Electrophoresis". *Surface Chem.*, Colloids, 111, (8), 64754, 1989.

Rodbard et al. "Estimation Of Molecular Radius, Free Mobility & Valence Using Polyacrylamide Gel Electrophoresis". Anal.Biochem, 40, 95–134, 1971.

Sambrook et al. Molecular Cloning. $2^{nd}$ Ed.(New York: Cold Spring Harbor Laboratory Press), 6.2–6.63, 1989.

Slater. "Stable Pattern Formation Of Determination Of Molecular Size By Pore Limit Electrophoresis". Analytical Chemistry, 14, (8), 1039–1041, Jul., 1969.

* cited by examiner

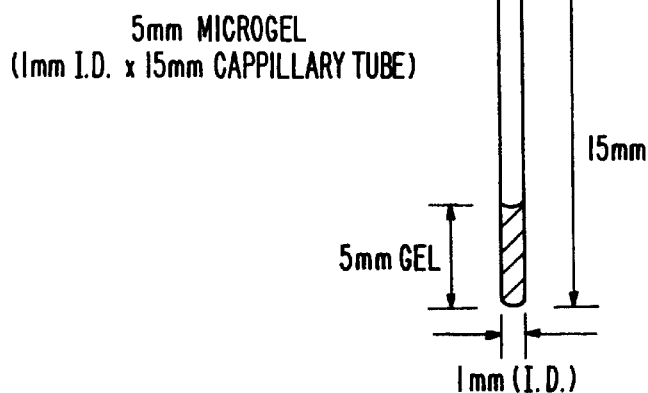
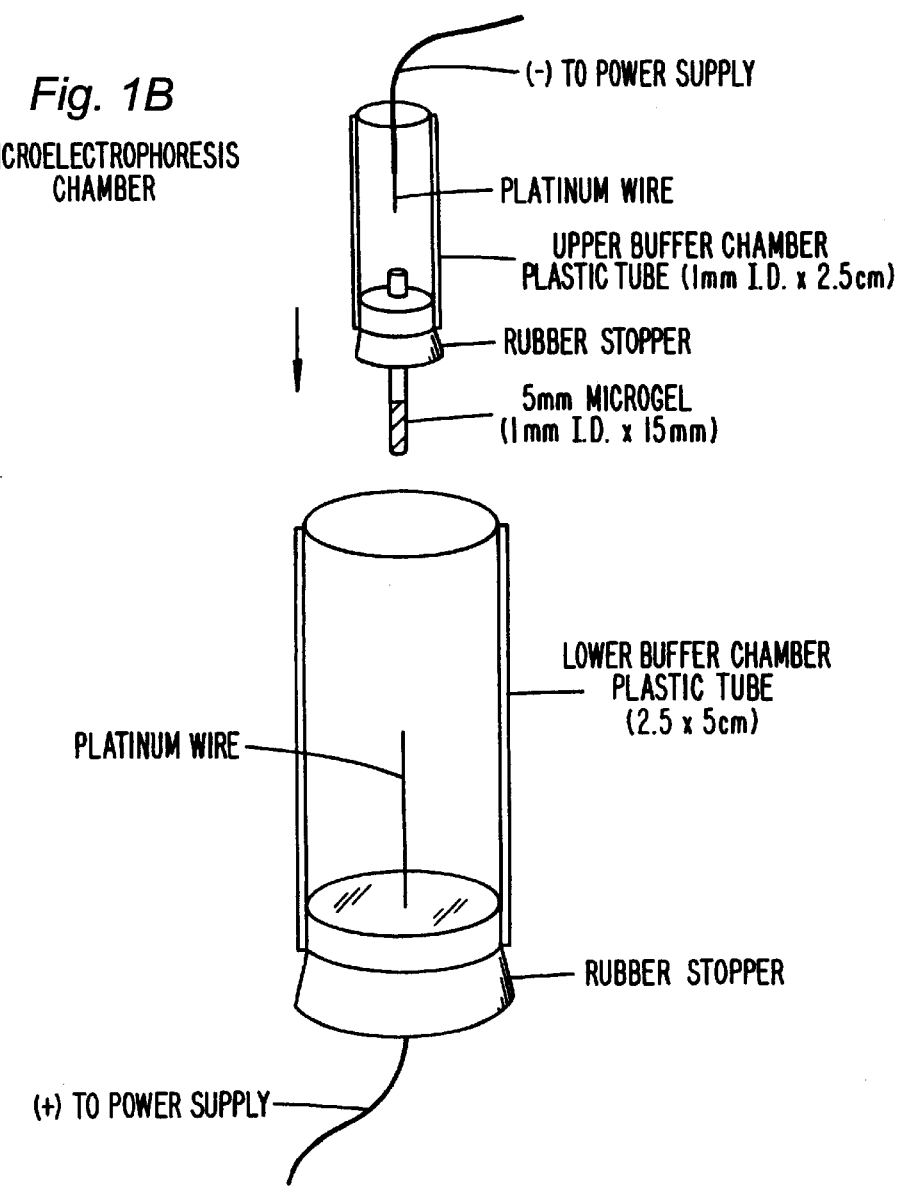

Fig. 6

ARRAY BASED ELECTROPHORETIC SYSTEM FOR THE ANALYSIS OF MULTIPLE BIOLOGICAL SAMPLES

This is a continuation of application Ser. No. 08/234,637 Apr. 28, 1994, now issued as U.S. Pat No. 6,013,166, which is a continuation of application Ser. No. 07/698,482, filed on May 9, 1991, now abandoned.

TECHNICAL FIELD

This invention relates to methodology for reducing the linear dimension necessary to carry out electrophoretic separations of nucleic acid fragments. Separations normally requiring many centimeters of running distance, can now be resolved in several millimeters. This novel methodology provides for microelectrophoresis, with the inherent advantage of significantly reduced separation times.

BACKGROUND

Electrophoretic analysis is a powerful and widely used technique in the fields of biochemistry and molecular biology. The advent of recombinant DNA technology, the rapid growth of the polymerase chain reaction technology, and the initiative to sequence the human genome have further stimulated its useful development, particularly for the separation of nucleic acids. Nucleic acid analyses are carried out on sample mixtures which range in size from oligonucleotides several nucleotides in length to large DNA fragments millions of base pairs in length. Agarose gel electrophoresis and polyacrylamide gel electrophoresis (PAGE) are the two main types of electrophoresis used for analysis of nucleic acids. In most cases the short to intermediate sized nucleic acid fragments [10 to 1000 base pairs (bp)] are separated in polyacrylamide slab gels arranged in vertical formats, and the intermediate to high molecular weight nucleic acid fragments (100 to 100,000 nucleotides) are separated in agarose slab gels arranged in a horizontal formats. A special technique called pulse field electrophoresis is used to resolve very large DNA fragments up to 5 megabases. In general, slab gels used in these procedures range from so-called mini-gels which are approximately 5 cm×5 cm to the more standard sized gels which are 20 cm×20 cm formats. These formats provide running distances of 5 to 20 centimeters in which the separations occur.

In the case of DNA sequencing, where resolution of DNA fragments varying by one nucleotide is required, polyacrylamide gels from 20 cm to 40 cm are commonly used, and in some cases gels as long as 100 cm have been used. Improvements in DNA sequencing using polyacrylamide slab gels has been achieved mainly by using thinner and lower percentage polyacrylamide gels. Presently, using the most optimal techniques and equipment (Applied Biosystems, Inc., Automated Fluorescent DNA Sequencer) a 300–400 base sequence determination on slab gel with a 25 cm running distance takes four to six hours to complete. More recently, a newer technique called capillary electrophoresis is being developed for DNA sequencing applications. This technique uses very narrow diameter capillary tubes (50 um to 100 um) containing low percentage polyacrylamide gels. Separations comparable to the slab gel formats can be carried out in 30 to 40 minutes. The improved speed with the capillary format comes primarily from being able to apply higher voltages to the very thin, low percentage polyacrylamide gel; however, gel lengths of 40 to 70 centimeters are still required to achieve the resolution. Thus, in the almost twenty years of development in electrophoretic techniques, the linear dimension or length of gel required for the high resolution separation of nucleic acid fragments has stayed approximately the same.

A few early attempts were made to investigate the potential for microelectrophoresis. Edstrom, (Biochem. Biophys. Acta, 22:378, 1956) first described a microtechnique for the electrophoretic separation of purine and pyrimidine bases along a silk thread. Matioli et al., (Science, 150:1824, 1965) have separated hemoglobin variants on polyacrylamide fibers. In this work, 20% acrylamide gels were used to separate hemoglobin variants from single cells. Hemoglobin molecules (MW ~64,000) with molecular radii of 2.66 nm are not pore size limited in 20% polyacrylamide gels, thus the separation occurs by the "normal gel sieving process". See Andrews, A. T. in "Electrophoresis: Theory, Techniques, and Biochemical and Clinical Applications", Oxford University Press, New York, chapter 2, pp. 5–74 (1986). As will be shown, the present invention is concerned with the microelectrophoretic separation of molecules whose molecular radius, stokes radius, or radius of gyrations are significantly greater than gel pore size.

Other separation systems have been described that were referred to as mini-gel electrophoresis, that emphasize separation of proteins. Grossbach, U. in "Electrophoresis and Isoelectrofocusing in Polyacrylamide Gels", eds. Allen et al, Walter de Gruyter, New York, p.207 (1974), describes separation of proteins in 50 um to 100 um diameter capillaries tubes which were 2.5 centimeters long, using standard gels and buffers. Neuhoff et al., Biochem J., 117:623 (1970) and Bispink et al, in "Electrofocusing and Isotachophoresis", eds. Radola et al, Walter de Gruyter, New York, p.125 (1977) describe analytical PAGE on proteins carried out using 5 centimeter capillary tubes. "Micro versions" of polyacrylamide slab gels have been prepared on 75 mm×25 mm microscope slides [Maurer et al, Anal. Biochem., 46: 19 (1972)] and on 82 mm×102 mm glass microscope slides [Matsudaira et al, Anal. Biochem., 87:386 (1978)]. In all of the above work, gel lengths or running distances are at least five to forty times longer than described by the present invention; the above described systems are more accurately described as mini-gels or scaled down version of large gels. In the above work, standard gel formulations were used. That is, gel formulations in the above systems do not significantly deviate from what is used for the corresponding large scale separation. More importantly, in the above systems the molecules (proteins) are being separated by the "normal sieving process" which occurs for molecules which have a molecular radius that is smaller than the gel pore size of the separation medium. Finally, the term "micro" refers more accurately to the width, diameter, or thickness of the gels, rather than to the length or linear dimension.

Gradient gel electrophoresis is a technique in which a gel matrix having an increasing concentration of polyacrylamide (3% to 40%) along the separation axis is used to separate macromolecules in a wide range of sizes. In gradient gel electrophoresis the rate of migration of the components through a gel gradient varies inversely with time. After a sufficient electrophoresis time a stable pattern develops in which the different components continue to move slowly but their relative positions remain constant. That is, as the components reach the gel pore size that is close to their own size (molecular radius), their terminal velocity approaches zero. See, for example, Andrews, A. T., in "Electrophoresis: Theory, Techniques, and Biochemical and Clinical Applications", Oxford University Press, New York, chapter 4, pp. 93–116 (1986). A great deal of theoretical work and application of techniques for determining molecular weights and molecular radii of proteins has been described by Rodbard et al, Anal. Biochem., 40:95–134 (1971); Manwell, Biochem. J., 165:487–495 (1977); and Campbell et al, Anal. Biochem., 129:31–36 (1983).

DNA separation by using gradient gel electrophoresis has been described by Jeppesen, Anal. Biochem., 58:195–207 (1974). DNA fragments of molecular weights from about $7 \times 10^4$ daltons (114 bp) to about $14 \times 10^6$ daltons (21,226 bp) were separated on linear gradient polyacrylamide gels having concentrations from 3.5% to 7.5% or from 2.5% to 7.5% with a crosslinker (C) concentration ranging from 2.5% to 5%. The gels described by Jeppeson were 14 cm long×14 cm wide×0.3 cm in thickness. Electrophoresis was carried out at 10 volts/cm from 16 to 20 hours, until the DNA fragments reached terminal velocities that approached zero. According to Jeppesen, maximum separation is achieved as the fragments approach zero velocity (gel pore limit), and further increase in running time results in little change in band position. Table 1 below shows the approximate acrylamide concentration (%T) or gel pore limit at which point the separated DNA fragments reached terminal velocities:

TABLE 1

| DNA Fragment | MW (daltons) | Fragment Size (bp)[1] | % Gel (% T) Terminal Velocity Reached |
|---|---|---|---|
| Lambda DNA/R1 | | | |
| (1) | $13.7 \times 10^6$ | 21,226 | 3.8 |
| (2) | $4.5 \times 10^6$ | 7,421 | 3.9 |
| (3) | $3.5 \times 10^6$ | 5,804 | 3.9 |
| (4) | $3.0 \times 10^6$ | 5,643 | 3.9 |
| (5) | $3.5 \times 10^6$ | 4,878 | 4.0 |
| (6) | $2.3 \times 10^6$ | 3,530 | 4.2 |
| SV40 DNA/R | | | |
| A | $6.5 \times 10^5$ | ~1,000 | 5.2 |
| B | $4.2 \times 10^5$ | ~646 | 5.9 |
| C, D | $3.2 \times 10^5$ | ~492 | 6.5 |
| E, F | $2.3 \times 10^5$ | ~354 | 6.7 |
| G | $2.1 \times 10^5$ | ~323 | 7.0 |
| H | $1.2 \times 10^5$ | ~185 | 7.2 |
| I | $1.0 \times 10^5$ | ~154 | 7.3 |
| J | $8.7 \times 10^4$ | ~134 | 7.4 |
| K | $7.4 \times 10^4$ | ~114 | 7.5 |

[1]Lambda DNA/R1 fragments are the double-stranded (ds) DNA fragments produced by an Eco RI restriction endonuclease digestion of lambda DNA having sizes described by Phillipsin et al, J.Mol.Biol., 123:371 (1978). SV40 DNA/R fragments are the ds DNA fragments produced by an endonuclease R (Hind III) digest of SV40 DNA and having sizes estimated from the given molecular weights.

The Jeppesen work demonstrates two important points: (1) that in large gel formats the further separation of DNA fragments larger than their pore limit size is not observed; and (2) that acrylamide gel concentrations (%T/%C) only up to certain identified levels are useful to separate a given range of DNA fragments by the "normal gel sieving process".

Nucleic acid fragment analysis using denaturing polyacrylamide gels was described at least by Maniatis et al., Biochemistry, 14:387 (1975). Maniatis (1975) described the relative electrophoretic mobilities of RNA and DNA molecules having chain lengths of 10–150 nucleotides (nt) when separated in 12% polyacrylamide/3.3% crosslinker (N,N'-methylene bisacrylamide) (12%T/3.3%C) gels containing 7 M urea (denaturing gel), using gel dimensions of 20 cm×20 cm×0.15 cm and running conditions of 1X TBE buffer for several hours at a constant voltage of 10 volts per centimeter (10V/cm) in the vertical direction. Sanger et al., Nature, 265:687 (1977), showed the relative mobility of PhiX174 DNA/Hind II fragments with chain lengths of 1,049, 770, 609, 495, 393, 335/340/345 (unresolved triplet), 297/291 (unresolved doublet), 163, and 79 nt in 5% polyacrylamide gel containing 98% formamide. Sauger's gel dimensions were 20 cm×20 cm and the gels were run in 0.02 M phosphate buffer. Maniatis et al., in "Methods in Enzymology", vol. 65, part 1, eds. Grossman et al, Academic Press, New York, p 299 (1980), recommends the above general conditions for separation of short to intermediate size DNA and RNA fragments under denaturing conditions.

Sambrook et al., in "Molecular Cloning: A Laboratory Manual," 2nd edition, Cold Spring Harbor, New York, pp. 6.2 to 6.63 (1989), and the references contained within, recommend the following gel concentrations and conditions for separating nucleic acid fragments on agarose gels having fragment sizes in the range of 100 to 60,000 nt at the following percentages:

TABLE 2

| Agarose in Gel (%) | Range of Sizes for DNA Molecules (nt) |
|---|---|
| 0.3 | 5,000–60,000 |
| 0.6 | 1,000–20,000 |
| 0.7 | 800–10,000 |
| 0.9 | 500–7,000 |
| 1.2 | 400–6,000 |
| 1.5 | 200–3,000 |
| 2.0 | 100–2,000 |

Following the above recommendations, agarose gel electrophoresis of DNA was generally carried out in the horizontal direction using slab gels ranging from 14 to 20 centimeters in length. It was generally recommended that the gels be run at no more than 5 V/cm. Depending upon the degree of resolution required and the voltage utilized, running times for agarose gels varied from one to sixteen hours. However, agarose gels have very poor resolution below 100 nt, and only intermediate resolution at higher chain lengths (>100 nt). Therefore, agarose gels are more frequently used for Southern analysis or restriction fragment analysis, rather than for DNA sequencing applications which requires high resolution of shorter chain lengths.

Very large linear ds-DNA molecules were found to migrate through agarose gels at the same rate. The limit of resolution was reached when the radius of gyration of the linear DNA duplex exceeds the pore size of the gel. At that point the DNA can no longer be sieved by the gel according to size but must now migrate end-on through the narrow pores. This process of end-on migration is known as "reptation". Sambrook et al., in "Molecular Cloning: A Laboratory Manual" 2nd edition, Cold Spring Harbor, New York, pp. 6.2 to 6.63 (1989). One solution to the problem of separating large DNA molecules is a technique called pulsed field electrophoresis developed at least by Schwartz et al., Cell, 37:67 (1984). In this method, pulsed, alternating, orthogonal electric fields are applied to agarose gels. The large DNA molecules become trapped in their "reptation tubes" and can make no further progress through the gel until they have reoriented along the new axis of the electric field. The larger DNA molecules require a longer reorientation time; the smaller molecules with reorientation times less than the pulse begin to separate according to size. Pulse field electrophoresis involves large agarose gel formats, complex electrode arrangements, and very long running times to achieve separations. Pulse field electrophoresis provides important background information for the present invention because it shows; first, that very large DNA molecules which are larger than gel pore size are not separated using regular large scale gel formats and procedures; and second, that the solution to the "reptation problem" is the complicated and extremely long process described above.

Sambrook et al., in "Molecular Cloning: A Laboratory Manual", 2nd edition, Cold Spring Harbor, N.Y., pp. 6.2 to 6.63 (1989), and the references contained within, recommend the following gel concentrations and conditions for separating nucleic acid fragments on non-denaturing polyacrylamide gels in the following concentration ranges where the DNA fragments have sizes in the range of 6 to 2000 nt in length:

TABLE 3

| Acrylamide (% T/% C) | Range of Sizes for DNA Molecules (nt) |
| --- | --- |
| 3.5% T/3.3% C | 100–2000 |
| 5.0% T/3.3% C | 80–500 |
| 8.0% T/3.3% C | 60–400 |
| 12.0% T/3.3% C | 40–200 |
| 15.0% T/3.3% C | 25–150 |
| 20.0% T/3.3% C | 6–100 |

Following the above recommendations, gels were typically run in vertical format and over lengths from 10 to 100 centimeters depending on the resolution required. Gels were run in 1X TBE buffer at voltage gradients between 1 V/cm to 8 V/cm. Higher voltages were not recommended due to the problems associated with overheating. Runs generally took from one to twelve hours depending upon resolution required. Strand-separating polyacrylamide gels were recommended for nucleic acid fragments below 1000 nt in length, in particular for sequencing by the Maxam-Gilbert procedure [Maxam et al., *Proc. Natl. Acad. Sci. U. S. A.*, 74:560 (1977)] and for hybridization to low abundance RNA's (Maniatis et al., in "Molecular Cloning: A Laboratory Manual", Cold Spring Harbor, N.Y., pp. 179–185, 1982). For DNA fragments greater than 200 nt in length, 5%T/2%C gels were recommended; while 8%T/3%C gels were recommended for fragments less than 200 nt in length. These gels were typically run in 1X TBE and at 8 V/cm.

Sambrook et al., in "Molecular Cloning: A Laboratory Manual", 2nd edition, Cold Spring Harbor, N.Y., pp. 6.2 to 6.63 (1989), and the references contained within, recommend the following gel concentrations and conditions for separating nucleic acid fragments on denaturing polyacrylamide gels containing 7 M urea, where the duplex DNA fragments are in the 10 to >200 nt range:

TABLE 4

| Acrylamide (% T/% C) | Range of Sizes for DNA Molecules (nt) |
| --- | --- |
| 4% T/5% C | >200 |
| 5% T/5% C | 80–200 |
| 8% T/5% C | 40–100 |
| 12% T/5% C | 10–50 |

Following the above recommendations, denaturing gels were typically run at 20 V/cm in 1X TBE, and it was typically recommended that the DNA fragments be allowed to migrate the full length of the gel in order to obtain maximum separation. It should be pointed out that the agarose and polyacrylamide gel formulations discussed above have been frequently used in so-called mini-gel formats, which are generally about five to ten centimeters in length. Mini-gels represent a two to four fold size reduction in the linear dimension, and are basically only scaled down versions of the systems described above. As will be discussed below, the high resolution necessary for DNA sequencing is not achieved when accepted large-scale procedures are scaled down to mini-gel format. More importantly, as will be demonstrated by the present disclosure, true microelectrophoresis which produces the required resolution can not be obtained by simply scaling down large scale procedures.

In the case of DNA sequencing, where separation of DNA or RNA fragments differing by a single nucleotide is required, electrophoresis techniques with speed and high resolution are required. Maxam et al developed the chemical cleavage sequencing method [*Proc. Natl. Acad. Sci. U. S. A.*, 74:560 (1977)] and used the following polyacrylamide compositions and procedures for sequencing gels: for DNA sequences from 1 to 30 nt a 20%T/5%C (8.3 M Urea) gel was used; for sequences from 25 to 250 nt a 8%T/5%C (8.3 M Urea) gel was used; and for sequences greater than 250 nt a 6%T/5%C gel was used. The gels were 20 cm×40 cm in width and length, respectively, and gel thicknesses of 1.5 mm, 0.5 mm, and 0.3 mm were used. The thinner gels of 0.3 mm were typically preferred due to their capacity to withstand higher voltages and faster run times. Sequencing gels were run in 1X TBE buffer at voltages of 25 V/cm for 1.5 mm gels, and 50 V/cm for the 0.3 mm gels. See, for example, Maxam et al., in "Methods in Enzymology", vol. 65, part 1, eds., Academic Press, New York, p. 499 (1980). Depending on the separation required, resolution of the DNA fragments in the sequencing reactions takes many hours to complete.

More recently Barker described in "Nucleic Acid Sequencing: A Practical Approach", eds. et al, IRL Press, New York, Chapter 5, 117 (1989), the use of one meter long gels for DNA sequencing by the Maxam and Gilbert method. Early workers carrying out the primed synthesis DNA sequencing method [Sanger et al., *Proc. Natl. Acad. Sci. U. S. A.*, 74:5463 (1977)] used the following polyacrylamide compositions and procedures for sequencing gels: for DNA fragments from 30 to 250 nt an 8%T/5%C (7 M urea) gel was used, and for fragments >250 nt a 6%T/5%C (7 M urea) gel was used. See, for example, Smith in "Methods in Enzymology", vol. 65, part 1, eds. Grossman et al., Academic Press, New York, p. 560 (1980); and Sanger et al, *FEBS Lett.*, 87:107 (1978). The gels were 20 cm×40 cm, and 0.35 mm in thickness. Gels were run at 30 to 40 volts/cm and take many hours to complete. In general, as DNA sequencing developed, the trend in gel formulations and size of polyacrylamide slab gels progresses toward thinner gels and slightly less concentrated gels, but there were no significant reductions in the length of these sequencing gels. See, for example, Andrews in "Electrophoresis: Theory, Techniques, and Biochemical and Clinical Applications", Oxford University Press, New York, chapter 6, pp. 148–177 (1986); and "Nucleic Acid Sequencing: A Practical Approach", eds. Howe et al, IRL Press, New York, (1989), and references contained within.

Automated DNA sequence analyzers based on fluorescent detection have become available in the past few years. Workers at Applied Biosystems, Inc. (ABI) and the California Institute of Technology have developed an automated DNA sequencer which uses four fluorescent dye-labelled primers. Connel et al. *BioTechniques*, 5:342 (1987). Each of the dye-labelled primers is paired with one of the four dideoxynucleoside triphosphate chain terminators, and used in the Sanger sequencing method to introduce fluorescent labels into DNA fragments produced by primer extension. More recently, fluorescent dideoxynucleotide nucleotide derivatives have become available for use on the ABI sequencing machines, thus eliminating the need for fluorescent primers. The fluorescent fragments produced in the separate A, C, G, and T reactions are combined and can be co-electrophoresed in the same lane and distinguished during electrophoresis by the color of their fluorescence. The system has an argon-ion laser which excites each of the fluorescent fragments as they pass through a small area near the bottom of the separation gel. The fluorescent signal from the fragments is focused by a collection lens through a four wavelength selectable filter onto a photomultiplier tube (PMT). The digitalized signal from the PMT is transferred directly into a computer for subsequent processing and display.

After computer processing, the sequence information is presented graphically as a linear array of colored peaks with the actual base sequence (A, T, G, & C) given above each peak. The system uses 6%T/5%C (7 M Urea) polyacrylamide gels, 0.4 mm or less in thickness. An 8% gel is recommended for better resolution closer to the primer; while a 4% gel can be used for better downstream resolution (>400 bp). A running distance of 25 cm is required to achieve the appropriate resolution of the fluorescent DNA fragments. Generally, electrophoresis is carried out at 30 to 40 volts/cm, with sequences up to 500 bases being determined in a 8 to 12 hour run. Heiner et al, in "Nucleic Acid Sequencing: A Practical Approach" eds. Howe et al, IRL Press, New York, Chapter 8, pp.221–235 (1989).

Another automated DNA sequencer using fluorescent detection has been developed at the E. I. du Pont Company as described by Prober et al. *Science,* 238:336 (1987). This system uses an 8%T/5%C (7M Urea) gel in a 20 cm wide by 40 cm long by 0.3 mm thick format. Thus, the state of the art for the high resolution separation of DNA fragments on polyacrylamide slab gels for sequencing purposes: (1) uses gel concentrations of about 6%T/5%C, (2) requires gel lengths of at least 25 to 40 cm, (3) is limited to voltages of 40 volts/cm, and (4) requires many hours of running time.

A newer technique, which may be considered second generation DNA sequencing technology, is capillary gel electrophoresis. Morris et al, U.S. Pat. No. 4,909,919; Luckey et al., *Nucl. Acids Res.,* 18:4417 (1990); Drossman, *Anal. Chem.,* 62: 900 (1990); and Guttman et al., *Anal. Chem.,* 62:137 (1990). Capillary electrophoresis involves the use of very fine glass capillary tubes 50 to 100 um in diameter and 40 cm to 100 cm in length. Capillary gel electrophoresis has an advantage in that much greater electric fields may be applied, because of the reduced Joule heating in the small diameter capillary. This results in as much as a 14 fold faster separation speed over conventional slab gel methodologies. Thus, whereas a DNA sequencing separation of 300–400 bases run at 30 to 40 volts/cm on a 40 cm slab gel takes 7–8 hours to complete, the same separation on a 40 cm capillary gel run at over 400 volts/cm takes only 30–40 minutes to complete. The lower concentration gel [3.2%T/2.7%C (7M Urea)] used in the capillary columns is one factor in the improved separation speed.

Thus while capillary gel electrophoresis represents a significant improvement in separation speed, the gel lengths necessary for achieving the separation are still 40 to 70 cm long, and very low polyacrylamide concentrations are utilized.

BRIEF SUMMARY OF THE INVENTION

It has now been discovered that electrophoretic separation of macromolecules can be accomplished in relatively short gel support (matrix) distances referred to herein as separation patterns by using matrices having substantially higher gel concentrations than previously before in a format that allows for the application of substantially larger electric fields in the range of 5 to 100 volts per "millimeter" of gel support.

Thus in one embodiment the invention contemplates an electrophoretic method to effect differential net migration, the extent of said migration being dependent on molecular size, of electrically charged linear macromolecules through a gel support in a single dimension, which method comprises subjecting electrically charged linear macromolecules applied to a gel support to an electric field oriented along a single axis within the gel for a time period sufficient to effect migration in the direction of the oriented field and form a separation pattern in order of the respective molecular weights of the linear macromolecules in a distance of about 0.5 to 20 mm, said gel support comprising about 3 to about 40 percent acrylamide, said electric field being applied in an amount of about 5 to about 100 volts per millimeter of gel support along the axis length, and said gel support having a width perpendicular to said axis of about 0.1 to 1.5 millimeters.

In preferred embodiments, the gel support is in a capillary tube format having an inner diameter of about 0.25 to 1.0 millimeters.

Depending on the size of the linear macromolecules to be separated, the invention describes preferred gel supports of different ranges of acrylamide and crosslinking bis-acrylamide.

Preferred gel support lengths are also described as being less than 25 millimeters (mm), preferably between 0.5 to 20 mm and more preferably about 2 to 15 mm. Within these gel support lengths, and by virtue of the separation pattern resolution and speed of resolution afforded by the present invention, preferred separation patterns are described having lengths of 0.5 mm to 2.0 cm when practicing the methods of the present invention.

In another embodiment, the present method describes electrophoretic separations where the applied electric field is about 15 to 50 volts per mm of gel support length.

BRIEF DESCRIPTION OF THE DRAWINGS

FIG. 6 illustrates a 40X image showing separation of fluorescently labeled 18-mer, 21-mer, 23-mer, and 32-mer oligonucleotides separated on a 13 mm 26%T/6%C micro-gel as described in Example 4.

DETAILED DESCRIPTION OF THE INVENTION

A. Definitions

Figure 1C:
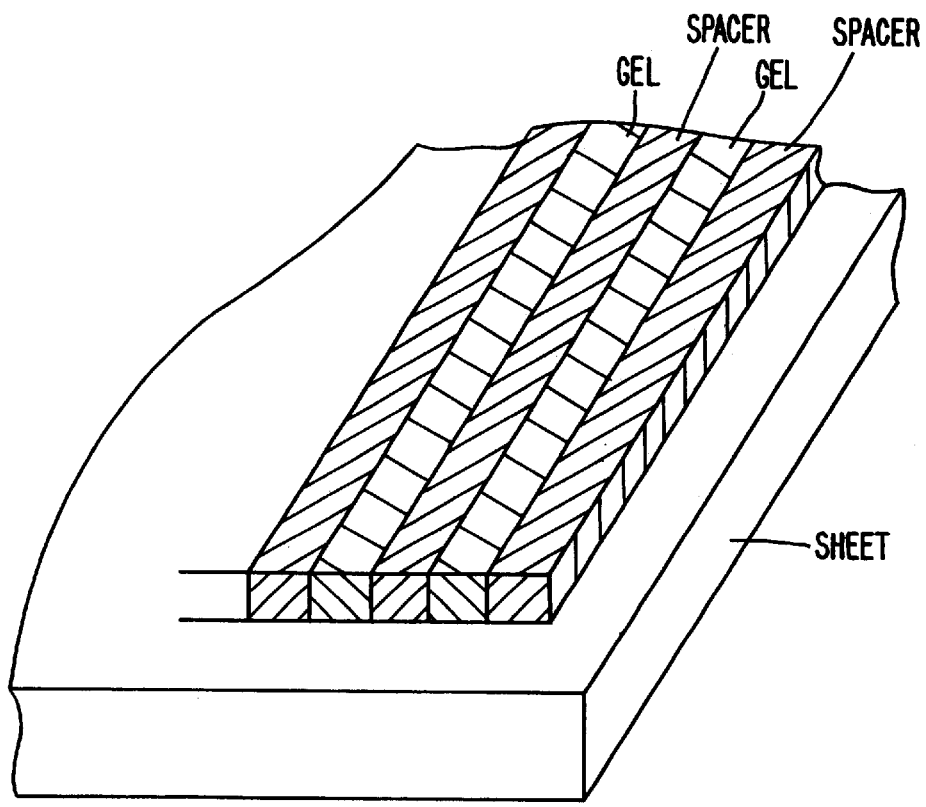
FIG. 1 in panel A illustrates the capillary tube micro-gel of this invention. Panel B shows the microelectrophoresis chamber as described herein. Panel C shows an array format for the electrophoretic system. Panel D shows an array format for a parallel array of capillary tubes.

Homogeneous gel: a gel that is completely composed of one acrylamide concentration.

Gradient gel: a gel where the acrylamide concentration varies from the top of the gel to the bottom of the gel.

Normal sieving process: a normal process occurring in acrylamide and agarose gels, by which molecules smaller than their pore size are separated.

Gradient gel process: a process in which molecules begin to reach terminal velocities as they approach gel pore size equivalent to their own size (molecular radius).

Pulse field process: a separation process used to resolve high molecular weight DNA fragments that are much larger than the gel pore size that involves applying pulsing and alternating orthogonal electric fields to effect migration of fragments down a long gel medium.

B. Methods for Separating Macromolecules

General Discussion

The present invention describes methodology for performing a micro-formatted electrophoretic separation of nucleic acids fragments in relatively highly concentrated and crosslinked gels. The homogenous polyacrylamide gel compositions used to obtain the resolution for a particular range of DNA fragments are of much higher concentration and crosslinking than previously described and used by those practicing the art. The novel methodology described by the present invention involves a separation process occurring inside gel pores whose diameters are significantly smaller than the molecular radius or radius of gyration of the linear DNA fragments being separated. This process is different than the "normal gel sieving process", the "gel gradient process", or the "pulse field process" as previously discussed in the Background. This new process is both unexpected and un-obvious because, as discussed before, effective separations do not occur for DNA molecules larger than gel pore size.

This point is demonstrated clearly by comparing (1) the gradient gel results for the SV40 DNA/Endo R fragments described by Jeppesen (shown in Table 1 in the Background section) with (2) the micro-gel results disclosed for the PhiX174 DNA/Hae III fragment in Examples 1, 2, and 3 herein. Both the SV40 DNA/Endo R fragments (114 to 1000 bp) and the PhiX174 DNA/Hae III fragments (72 to 1,353 bp) are in the same size range. The Jeppesen gradient gel results show the largest fragment reaching its terminal velocity at approximately a 5.2% gel and the smallest fragment reaching its terminal velocity at approximately a 7.5% gel.

Terminal velocities are reached when the macromolecules being resolved no longer separate according to the normal gel seiving process. This condition exists where the average pore size of the matrix is smaller than the effective molecular radius of the macromolecules being resolved on the gel medium (matrix). According to the present invention, a new level of electrophoretic separation is accomplished when higher voltages are applied than were previously utilized to a gel having matrix pore sizes relative to macromolecular radii that under conventional voltages. would result in "terminal velocity" type electrophretic conditions.

Methods for determining gel matrix pore sizes and molelcular radii are generally well known. See for example the teachings of Jeppesen, Anal. Biochem., 58: 195–207 (1974); Manwell, Biochem. J., 165:487–495 (1977); and Campbell et al, Anal. Biochem., 129:31–36 (1983). Jeppesen teaches that the gel percent at which terminal velocity is reached defines the average pore size of the gel matrix in terms of the molecular radius of the macromolecule whose migration stops (i.e., reaches terminal velocity). Thus Table 1 provides teachings for correlating acrylamide gel percents to the maximum nucleic acid molecule able to enter the gel support by the normal seiving process.

In the present methods, electrophoresis of macromolecules occurs in gels having matrix average pore sizes that are smaller than the macromolecule's molecular radii due to the combination of electric field strength, average pore size of the matrix, and gel dimensions to accomodate minimal gel overheating.

The PhiX174/Hae III fragment separation results shown in Examples 1, 2, and 3, describe the complete separation of the same size range of fragments in a 12%, 18%, and a 26% gel, in running times of 2 to 3 minutes. The process described by this invention now provides for the rapid separation of DNA molecules larger than gel pore size. The micro-scale format, the gel compositions, and running conditions (voltages, etc.) used in this novel methodology combine synergistically and lead to the resolution of the relatively large (in relation to pore size) linear DNA fragments as they migrate through the narrow pore structures. The following synergistic effects are involved in this process. The micro-gel format, which has inherently reduced Joule heating, allows high voltage gradients to be used to drive the separations in the relatively concentrated gels. The higher voltage gradients lead to faster separation times. The highly concentrated gels produce very narrow band widths with greatly reduced diffusion. The combination of effects leads to the highly efficient separation process being observed.

The overall benefits of the new technique are: (1) the linear dimension necessary to carry out separations is significantly reduced to the range of millimeters; (2) the highly resolved extremely narrow banding patterns are produced for a wide range of DNA fragments; (3) the separation times are extremely fast relative to the "normal sieving process"; most being complete in minutes; and (4) the complete high resolution separation pattern can now be quickly detected and imaged with high resolution and high sensitivity using an epiflourescent microscope and electronic imaging systems.

The present invention is particularly useful for nucleic acid fragment analysis including single or double stranded DNA molecules and fragments, RNA's, labelled (fluorescent, radioisotope, etc.) nucleic acid fragments, modified and un-modified synthetic oligonucleotides, and synthetic nucleic acid analogs. This methodology is also useful for separating other synthetic and natural macromolecules, including denatured proteins and polypeptides.

Thus, the present invention describes a method of separating macromolecules within a gel support that comprises subjecting the macromolecules to an electric field oriented in a direction along a single axis within and through the gel support.

The macromolecules are electrically charged macromolecules such as nucleic acid molecules (RNA; DNA) or proteinaceous molecules, such as detergent-protein complexes or other forms of protein having net charges proportional to their molecular weight, such that said charged macromolecules exhibit differential net migration within the gel support to an extent dependent on the molecular size of the macromolecules when subjected to the electric field.

The applied electric field is subjected to the macromolecules for a time period and in an amount sufficient to effect net migration of the electrically charged macromolecules in the direction of the electric field and within the gel support and to form a separation pattern comprised of a distribution and detectable separation of the macromolecules within the gel support. The separation pattern is oriented along the axis of the applied electric field and contains the charges marcomolecules ordered according to their respective molecular weights. By virtue of the resolution attainable in the present method, due principally to the small pore size provided by the gel support and the voltage settings used to form the electric field, the method forms a separation pattern in less than 2.0 centimeters, typically in about 0.5 to 20 millimeters (mm).

The gel support, in one preferred embodiment, is about 3 to 40 percent acrylamide, as described further herein below. other matrix materials are also contemplated for providing a matrix having the disclosed pore sizes.

The method includes subjecting the macromolecules to an electric field of about 5 to about 100 volts per mm of gel support along the axis length. Thus for gel supports, of about 5 mm, a voltage of about 5 to 100 volts per mm, or 50 to 1000 volts per centimeter are utilized.

The high voltages utilized in the present method can be tolerated without adversely affecting the gel support due to the thickness of at least one dimension of the gel support relative to the axis of migration. Thus, the method utilizes a gel support having a narrow width in the direction perpendicular to the axis length, preferably about 0.1 to 1.5 mm, more preferably about 0.25 to 1.0 mm in thickness, that facilitates minimum heating by the resistance produced by the gel support to the applied electric field. Particularly preferred are cylindrical gels that have a diameter equal to the above thicknesses.

Thus, the present invention describes a method for electrophoretic separation of a sample of electrically charged macromolecules that have been applied to a surface of a gel support and that are then subjected to an electric field as described herein. After the electric field has effected the desired net migration, a process referred to as electrophoresis, the separation pattern formed in the gel support is then detected by some evaluation means that allows for determining the relative location of each separated macromolecule species within the sample.

In a related embodiment the present method can be used for the isolation of a species of macromolecules from a sample by first electrophoresing the macromolecules and then isolating a discreet band (species of separated molecules) from the gel support, thereby isolating the species of macromolecules.

Other permutations of the present electrophoretic method will be apparent to one skilled in the art based on the present invention and the specific disclosures made herein.

1. Sample Preparation

Sample size (volume) and concentrations used in this new methodology are dependent, along with other factors, on (1) the dimension and geometry of the gel surface or microwell to which it is applied, and (2) to the inherent sensitivity of the detection system being used to analyze the banding patterns.

With regards to sample volume, and assuming sample concentration is appropriate, the ratio of the sample volume in nanoliters (nl) to gel surface area in square micrometers ($um^2$) should be kept as low as possible. For gel surface areas between $10^6$ $um^2$ to $10^4$ $um^2$, the sample volume to surface area ratio is 1 to 10,000, preferably 1 to 100,000 and more preferably 1 to 1,000,000. Thus for a one millimeter diameter micro-gel in capillary format having a surface area of 785,400 $um^2$, a sample volume of 100 nl can be used, but a 10 nl volume is preferred, and a 1 nl volume is more preferred. In practice the choice of sample volume used might depend on other factors. For example, if only a low resolution separation is required or a longer running time is acceptable, a larger sample volume can be used because the resulting band broadening can be afforded. However, gross overloading should be avoided (ratios lower than 1 to 1000). For very small sample volumes (<1 nanoliter), appropriate micro-dispensing equipment and techniques are needed.

In regards to sample concentration, if one assumes no limitation in ability to detect the resolved bands, then under a given set of conditions there is: (1) an upper level sample concentration which is not acceptable because of loss of band resolution; (2) a sample concentration range in which bands are adequately resolved, and (3) a general improvement in resolution as sample concentration decreases.

Preferred sample concentrations for use in the present invention are based on two sets of results presented herein using fluorescently labelled oligonucleotides or ethidium bromide stained ds-DNA fragments, which were each detected using the epifluorescent microscope and imaging system as described in the Detection and Example Section.

In one embodiment using fluorescent labels, fluorescent oligonucleotides were labelled with fluorescein or other equivalent fluorophores (Texas Red, Rhodamine, etc.) at one label per molecule. Synthetic oligonucleotides with a single fluorescein moiety per molecule covalently labeled at the 5'-terminal position can be commercially obtained from Synthetic Genetics, Inc. Mixtures of fluorescently labeled oligonucleotides can thus be prepared having concentrations ranging from $1\times10^{-13}$ to $5\times10^{-15}$ mole of individual oligonucleotide for sample volumes in the range of 1 nl to 100 nl. Higher sample concentrations will lead to band broadening, especially in the narrower (<0.5 mm I.D.) or thinner (<0.5 mm thickness) micro-gel formats. Lower amounts of sample can be used if more sensitive detection is available, and/or higher quality or special optical arrangements which reduce fluorescent background are used.

In another embodiment using ethidium bromide (EtBr) stained ds-DNA fragments, the relative fluorescence of EtBr-stained DNA fragments increases with their size. This is because the longer fragments intercalate increasing amounts of ethidium bromide. Thus, at an equivalent concentration, a 1000 bp fragment might have 10 times stronger fluorescent signal than a 100 bp fragment. For ethidium bromide stained ds-DNA fragments in the 100 to 1000 bp range, in sample volumes of 1 nl to 100 nl, concentration ranges of from $5\times10^{-4}$ to $5\times10^{-16}$ mole of each fragment are recommended. For fragments >1000 bp, the relative amount of fragment in moles can be reduced proportionately to the increase in fragment size.

Samples at appropriate concentrations are generally made up in a loading buffer which contains 0.5X to 1X TBE buffer (1X TBE is 0.089M Tris, 0.089M Borate, 0.2 mM EDTA, pH 8.0) and 10% to 30% (V/V) glycerol (a small amount of bromphenol blue and xylene cyanol dyes may be added to the loading buffer if desired). In cases were ethidium bromide staining is required the dye is typically added at a concentration of about 500 nanograms (ng) per mililiter (ml). Other loading buffer formulations common in the practice of gel electrophoresis are also acceptable.

2. Gel Compositions

Gel compositions are an important part of the present invention in their application to separating a particular size range of DNA fragments in micro-gel formats. In all cases the gel concentrations are higher than would normally be expected for a given size range of DNA fragments. As was shown previously in discussing the Background Art, for "normal gel sieving", gel concentrations were previously being typically chosen to provide pore sizes larger than the radius of the molecules or radius of gyration being separated.

While homogeneous acrylamide gels are used as exemplary of the present invention, agarose, starch, and other natural and synthetic hydrogels are applicable in producing a gel matrix.

With regard to homogeneous acrylamide gels the following table gives the broad concentration range of %C [percent crosslinker (bisacrylamide) relative to total acrylamide monomers] that is acceptable for gels used in the present invention which range from 3%T to 40%T (total percent acrylamide and crosslinker) concentration.

TABLE 5

BROAD CROSSLINKER RANGE
% T Total Acrylamide/% C Crosslinker (Range)

| | |
|---|---|
| 40% T/(5–14% C) | to 35% T/(5–13% C) |
| 35% T/(5–13% C) | to 30% T/(5–12% C) |
| 30% T/(5–12% C) | to 25% T/(4–11% C) |
| 25% T/(4–11% C) | to 20% T/(4–10% C) |
| 20% T/(4–10% C) | to 15% T/(3–8% C) |
| 15% T/(3–8% C) | to 10% T/(2.5–7% C) |
| 10% T/(2.5–7% C) | to 5% T/(2.5–6% C) |
| 5% T/(2.5–6% C) | to 3% T/(2.5–5% C) |

With regard to homogeneous acrylamide gels the following table gives the broad concentration range of %C [percent crosslinker (bisacrylamide) relative to total acrylamide monomers] that are "optimal" for gels used in the present invention which range from 3%T to 40%T (total percent acrylamide and crosslinker) concentration.

TABLE 6

OPTIMAL GEL RANGE
% T Total Acrylamide/% C Crosslinker (Optimal Range)

| | |
|---|---|
| 40% T/(9–12% C) | to 30% T/(8–11% C) |
| 35% T/(9–12% C) | to 25% T/(6–10% C) |
| 20% T/(8–11% C) | to 20% T/(5–9% C) |
| 25% T/(6–10% C) | to 15% T(4–8% C) |
| 20% T/(5–9% C) | to 10% T/(3–6% C) |
| 15% T(4–8% C) | to 5% T/(2.5–5% C) |
| 10% T/(3–6% C) | to 3% T/(2.5–4% C) |

In the case of polyacrylamide gels, these can be prepared in similar manner and technique common to the art of electrophoresis. In general, fresh mixtures of the appropriate percentage acrylamide/bisacrylamide (%T/%C) solutions are made up in ½X to 1X TBE buffer. The highest purity reagents available should be used to prepare polyacrylamide gel solutions. As an example, 100 mls of a 26%T/6%C (non-denaturing) polyacrylamide gel solution would be made up as follows: 23.4 g of acrylamide and 1.6 g of N,N'-methylenebisacrylamide (bisacrylamide or crosslinker) are weighed out and dissolved in ~75 ml of distilled water. Now 10 ml of 10X TBE (108 g Tris-base, 55 g Boric acid, and 9.3 g sodium EDTA in 1000 ml distilled water) is added and the solution is brought to a volume of 100 ml.

Both denaturing and non-denaturing gels can be used in this methodology. Denaturing gels containing 6 to 7M Urea are preferred. Because micro-gel formats (capillary tubes or micro-slabs) are used, only small amounts of gel solutions (1 to 2 ml) need to be prepared for polymerization and pouring of micro-gels. Ammonium persulfate and N,N,N'N'-tetramethylethylenediamine (TEMED) are used to catalyze the polymerization process.

The preparation of 10 mm (26%T/6%C) micro-gels in 1 mm (I.D.) capillary tube format, will be used as an example of how to prepare a micro-gel. Several 100 ul, 1 mm (I.D.)×11.5 cm long capillary tubes (Drummond) are cut into 5.75 cm lengths using a capillary cleaving tool (Supelco # 2-3740). A volume of 1.5 ml of 26%T/6%C polyacrylamide/bisacrylamide solution (room temperature) is placed in a small test tube. The solution is de-gassed by placing it under a vacuum for about 30 seconds. After de-gassing, 5 ul of a fresh ammonium persulfate solution (1 g/1.5 ml distilled water) is added and gently mixed for several seconds. Next, 3 ul of TEMED is added and mixed. This level of ammonium persulfate and TEMED initiates polymerization in about 2 to 3 minutes. About 250 ul of the solution is then quickly transferred to a 1.5 ml Eppendorf tube (conical bottom) Six of the 5 cm capillary tubes are placed vertically in the Eppendorf tube containing the 26%T/6%C polyacrylamide solution. The tubes are kept in vertical position while the solution fills them by capillary action to a height of about 2 to 3 cm. Within 2 to 3 minutes the gel begins to polymerize. It is important that the tubes be kept vertical until polymerization is complete, and then allowed to set for at least 30 minutes before using them. After polymerization is complete, the gel tops can be flushed with running buffer (½X to 1X TBE) and then cut into appropriate lengths. The capillary cleaving tool is used, and the tubes are first cut carefully 5 to 10 mm above the gel top for the upper buffer chamber, and then at the bottom to produce an actual gel length of 10 mm. The tubes should be kept submerged in running buffer until they are ready to be used for micro-electrophoresis.

3. Micro-Gel Formats and Geometry

The micro-gel formats are a synergistic part of the methodology of this invention which allows DNA fragments and other macromolecules to be separated within pore structures that are smaller than their molecular radius or radius of gyration. Micro-gels can be prepared in either capillary tube, micro-slab, or microchanneled formats. The sizes, lengths, and diameters and thicknesses are to be used with the sample volumes discussed above and the voltage gradients and other conditions discussed below. It is important to point out that ultra-micro separations on gels <0.1 mm in diameter or thickness could be carried out, however, special devices and techniques would be required to fabricate the gels and carry out the ultra-micro sample applications. Thus, this methodology is not inherently limited to the micro-gel scales being described in more detail below.

For single sample applications, glass capillary tubes from 5 to 27 mm long and from 0.1 mm to 1 mm inner diameter (I.D.) are appropriate. The "actual gel length" within the tube will be shorter, since from 2 to 10 mm of the upper area is used for sample application and as an upper buffer chamber; or to hold a piston type mold for preparing flat gel surfaces or sample micro-wells (see FIG. 1). The "actual gel length" for micro-gels can range from 1 to 25 mm, however gels from 2 to 15 mm are more ideal. If longer and thicker diameter tubes (>1 mm I.D.) are used, then Joule heating dissipation is slower, and the gel and separation process may begin to be adversely effected by overheating. Wider I.D. tubes or channels can be used, but require lower voltages and slower run times, and therefore are less preferred. Also, thicker gels may lead to loss of detection sensitivity, by increasing background (autofluorescence, etc.).

Narrower tubes or microcapillaries (<0.1 mm) can be used, but special ultra-micro sample application devices and techniques are required. The choice of actual gel length (separation matrix) is dependent upon the size range of DNA fragments and the level of resolution that is required. In general, for the separation of a large range of DNA fragments from 25 to 5,000 bp, that require only low to intermediate resolution, a 1 mm I.D. gel having an actual gel length of 2 to 10 mm is appropriate, with a 5 mm length being optimal. For separation of a range of fragments (e.g., 10 to 500 bp) requiring high resolution (i.e., separation of fragments that differ by one nucleotide) a 1 mm I.D. gel having an actual gel length of 5 to 20 mm is appropriate, with a 15 mm length being optimal. For a narrower range of fragments a gel length of 10 mm can be used to produce high resolution. It should be pointed out that in many cases, the full gel length is not required for the complete separation of the DNA fragments (see Examples); and the gel length used is determined more by the ease in preparing and manipulating a slightly longer micro-gel. Thus, it is convenient to refer to the length of the separation pattern rather than the actual gel length. The separation pattern length is the distance from the top of the gel to the smallest macromolecule migrating in the matrix and forming the pattern of separated macromolecules in the gel matrix after electrophoresis.

In further regard to gel lengths, it should be pointed out that conditions do exist under which longer gels could be used. If relatively smaller diameter or thinner gels are used, and/or lower voltages are applied, and much longer separation times are acceptable, then gels longer then 25 mm could be used. However, now the advantage of rapid separation times and compact banding patterns suitable for imaging detection would be lost.

For multiple sample applications, micro-slabs or micro-channeled arrangements can be used. These can be fabricated from thin glass sheets (microscope cover slips), using plastic or glass spacer materials, or specially fabricated microchannelled glass, or a parallel array of capillary tubes. The lengths and thickness used in these formats would correspond to those in the above description of capillary formats; lengths in the range of 1 to 25 mm, and thicknesses of from 0.1 to 1 mm would be acceptable. Thinner gel formats (<0.1 mm) could be used if devices and techniques for fabrication and ultra-micro sample application are available. The overall width of these formats would be determined by the number of sample lanes; with 10 lanes being a typical number of lanes. The width of the sample lanes would be determined by the gel thickness and sample volume to be applied. In general, for these types of formats with gel thicknesses of 0.1 to 1 mm, lane widths from 0.1 mm to 1 mm are contemplated. It is desirable to have the multiple sample arrangement (e.g., 10 lanes) so that the whole array of samples can be simultaneously detected and imaged in the field provided by 4X to 10X microscope objectives (40X to 100X magnification). The advantage in this is that the complete separation of 10 or more samples could be detected and imaged simultaneously.

An important aspect of micro-gel electrophoresis involves the relative flatness of both the top of the gel where the sample of macromolecules first enters the gel matrix during the beginning of electrophoresis, and the bottom of the gel. This flatness is important for several reasons. The first reason involves the nature of the micro-separation process which produces highly compact bands with very narrow band widths. Thus, any distortions, irregularities, and unevenness on the surface of the top of the gel where the macromolecules enter the gel leads to loss of band resolution. The second reason involves the aspect ratio of the micro-gels width to length. Because these are extremely short gels, slight differences in lengths between the top and bottom of the gel will have different voltage gradients. This will cause the sample at those locations to run at slightly different velocities leading to loss of band resolution. For example, a gel poured in a 1 mm I.D. capillary tube frequently has a meniscus, which produces a gel with a concave top. In a 5 mm gel the center may be 0.2 mm lower than the outer edges. This leads to a 4% difference in the voltage gradient between the center of the gel and the edges, which can cause some band broadening. For capillary formats this can be overcome by using a flat bottom piston mold (plastic, teflon, and the like) inserted into the top of the capillary tube during the polymerization process to produce a flat even surface on the top of the gel. Another aspect of micro-gel separation that leads to loss of band resolution involves the "edge effect". Distortion of the bands is observed where the glass and gel meet. Thus, an appropriate mold that produces a sample micro-well in the top of the gel having a flat well bottom is contemplated for reducing the edge effect problem. Particularly preferred is a mold that forms a square indentation (well) within the top surface of the gel and having a flat well bottom surface and positioned as to keep the sample from contacting the walls holding the gel.

4. Sample Loading

Sample loading for the methods of this invention involves the deposition of nanoliter quantities of sample on to a small area at the top of the gel or into a micro-well. Because of the nature of the micro-separation process care should be taken during the sample application process. Samples can be applied using a microliter or sub-microliter syringe (Hamilton # 701, # 7001N, and #7000.5N). The syringe should have a needle size of 25 gauge (0.5 mm) or smaller and a blunt tip (90° point). While delivery by hand can be carried out, a micromanipulator arrangement is preferred. In this arrangement the syringe and micro-gel are secured so the syringe needle can be carefully inserted, by a mechanical drive mechanism, into the upper part of micro-gel chamber above the top of the gel. A magnifying lens can be used to view the process enabling it to be carried out with more precision.

Before the sample is applied, the gel top is preferably first flushed with running buffer (½X or 1X TBE) and the upper micro-gel chamber (above the top of the gel) is left filled with running buffer. A syringe with a larger capacity (50 to 100 ul) can be used for this operation. Contact or abrasion to the top of the gel is preferably avoided. The micro-gel is preferably pre-electrophoresed prior to loading the sample, typically by subjecting the gel to 20 Volts/mm for 2 minutes.

The sample is then applied to the top surface or micro-well of the gel. To that end, the appropriate syringe is filled with sample to the appropriate preselected volume and the tip of the needle is slowly inserted into the upper chamber of the micro-gel and brought within a distance of 0.5 mm or less above the center of the top of the gel or micro-well. The sample is then slowly discharged from the syringe onto the top of the gel, with care taken not to agitate, dilute, or splash the sample against the walls of the micro-gel. The needle is removed slowly, and the micro-gel placed in the microelectrophoresis unit (see FIG. 1). The micro-gel is immersed completely into the lower buffer chamber so that some cooling can be provided to the gel. Care should be taken not to agitate the sample. Electrophoresis is carried out thereafter, and preferably immediately after sample loading without delay. The micro-gel is electrophoresed in the vertical position. Preferably the sample application is carried out with the micro-gel in the microelectrophoresis chamber. This requires a special arrangement of the sample application device (micromanipulator) with the microelectrophoresis unit. This arrangement has advantages in that the micro-gel need not be moved and electrophoresis could be started even faster. The appropriate voltage is applied for the time necessary to achieve the desired separation as described below. The micro-gel is then removed from the microelectrophoresis chamber and detection and imaging of the banding patterns is carried out as described below.

5. Electrophoresis

The micro-gel formats used in the present methodology allows much higher voltage gradients to be applied to higher gel concentrations, than could normally be used in conventional slab gel formats. This is because the short and relatively thin micro-gels have reduced Joule heating, and have the capacity to dissipate heat faster than larger scale gel formats. Thus, higher voltages can be used to drive the novel separation process of this invention leading to very fast separation of DNA fragments into highly compact microscopic banding patterns.

Figure 1D:
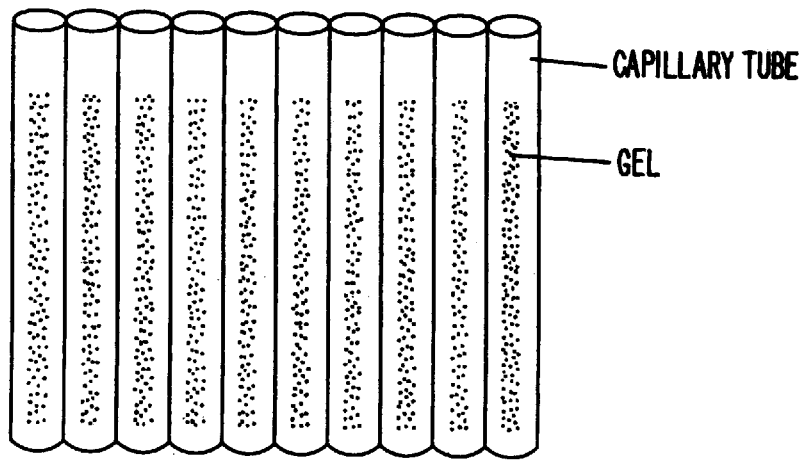

The microelectrophoresis chamber used for micro-gels in the capillary tube format is a relatively simple structure (FIG. 1). Running buffers used for microelectrophoresis ranged from ½X to 1X TBE; other buffers common to the art of electrophoresis would be acceptable. Voltages gradients applied to the micro-gels are given in units of Volts/mm, which is more applicable to micro-gels than Volts/cm. The Volts/mm units are determined by dividing the voltage reading on the power supply (BioRad Model 160/1.6 and model 500/200) by the "actual gel length", within the micro-gel capillary tube. For example, if a micro-gel has an "actual gel length" of 5 mm, and 200 volts is the reading on the power supply meter, then a voltage gradient of 40 Volts/mm was applied. By way of comparison 40 Volts/mm would be equivalent to 400 Volts/cm in a large scale gel format.

Actual gel length, as opposed to separation distance, is the length of the gel support, which length provides resistance to current and so must enter into calculations of voltage.

A wide range of voltage gradients (5 to 100 Volts/mm) can be applied to micro-gels depending upon the length (1 to 25 mm), diameter or thickness (0.1 to 1.0 mm), and polyacrylamide concentrations (shown in Table 6). In general, very low voltages (<5 Volts/mm) could still be applied, however resulting separation times will be very long. The use of very high voltage gradients may begin to cause band distortion. However, high voltages (including voltages >100 Volts/mm) could be used if they are switched on and off to allow time for heat dissipation to occur, and if relatively thinner gels are used. However, the more acceptable and optimal voltages are those that will produce separation with the appropriate level of resolution in a time period of 1 to 10 minutes. Table 7 below shows the range of acceptable voltages that can be used for the polyacrylamide concentration ranges indicated.

TABLE 7

VOLTAGE GRADIENTS

| Gel Concentration (% T/% C) | | Voltage (Volts/mm) |
|---|---|---|
| 40% T/(5–14% C) | to 30% T/(5–12% C) | 5 to 50 |
| 30% T/(5–12% C) | to 20% T/(4–10% C) | 7 to 60 |
| 20% T/(4–10% C) | to 10% T/(2.5–7% C) | 10 to 70 |
| 10% T/(2.5–7% C) | to 3% T/(2.5–5% C) | 12 to 100 |

6. Detection

Detection and imaging of the fluorescent banding patterns produced by microelectrophoresis of fluorescent DNA fragments can be carried out using an epifluorescent microscope combined with a high resolution imaging system. In general, fluorescent analysis has advantages over other methods (radioisotopes, chromogenic stains, etc.) for detecting DNA fragment bands in electrophoresis gels. First, it is more sensitive than most chromogenic stains, which usually require involved staining and washing procedures. Second, it is nearly as sensitive as radioisotope ($^{32}$P), which has the disadvantage of requiring special handling and disposal. Therefore, the detection of fluorescent DNA fragments would be a preferred method.

This new technology involves a unique synergistic combination of high resolution electronic imaging and epifluorescence with microelectrophoresis. High resolution electronic imaging technology [microchannel plates (MCP), intensified Charged Coupled Devices (CCD), cooled CCD, and Silicon Intensified Tubes (SIT)] provides the ability to easily carry out high resolution and sensitive detection and analysis of complex banding patterns in micro-gels. With these systems the complete electrophoretic separation pattern can be observed and recorded at any time during the process. Also, a large number of samples run in parallel micro-format arrangements could all be simultaneously analyzed with such systems. A further advantage is that these systems are relatively fixed with few moving parts. In addition to high resolution, some of the systems have the extremely high sensitivity which could be used to detect very low concentrations of fluorescent labelled DNA fragments (MCP systems can carry out photon counting imaging). These systems also have very fast image acquisition times (5–10 seconds), and high contrast ability (250 gray levels). All these properties give electronic imaging distinctive advantages. Electronic imaging makes it possible to know the relative position of all bands within the gel at any given time, and to better resolve the center band fluorescence in diffuse or overlapped bands. However, detection and analysis of fluorescent banding patterns in micro-gels could also be carried out by laser or other scanning fluorescent detection systems. Or a fixed fluorescent detection system that would simply monitor a position near the end of the gel and measure the fluorescent intensity as the bands past through could also be used.

The actual fluorescent detection and imaging of the micro-gel banding patterns were carried out using an AO Model 2070 Vertical Fluorescence epifluorescent microscope combined with a Hamamatsu C2400-97 Intensified CCD Camera and a Hamamatsu Argus-10 Image Processor. This particular system has a sensitivity of ~$10^7$ photon/cm$^2$.sec. Real time and processed images from the Argus-10 system was viewed on a Sony RGB monitor, and recorded using a Mitsubishi HS-328UR Video Cassette Recorder. Photographs were later made from the video tape recordings using a Sharp GZ-P21 Color Video Printer. The excitation source on the epifluorescent microscope was a 50 Watt Hg short arc lamp.

For the detection of fluorescein labelled oligonucleotides the epifluorescent microscope was filtered for excitation at 490 nm and emission at 520 nm. For detection of ethidium bromide fluorescence in ds-DNA fragments, the epifluorescent microscope was filtered for excitation at 450 nm and emission at 610 nm. Most observations and imaging were carried at either 40X magnification (4X objective and 10X eyepieces, ~5 mm field of view), or 100X magnification (10X objective and 10X eyepieces, ~1.2 mm field of view).

After completing the electrophoresis the micro-gel is laid on a microscope slide, and set on the microscope stage. Fluorescence bands can be visually observed at the higher concentrations of fluorescent fragments. With the imaging system the banding patterns can be observed in real time, or enhanced by collecting the image for several seconds. In any case, the image acquisition process takes less than one minute. The processed images can be presented in color, in positive white on black, or negative black on white form.

Other detection systems can be used based on refractive index detectors, conductance, light absorption and the like. Exemplary are the detection systems described in U.S. Pat. No. 4,909,919, which teachings are hereby incorporated by reference.

C. Gels For Separating DNA Fragments

The most novel part of this invention is that a set of conditions has been discovered by which DNA fragments can be quickly separated in micro-gel formats in polyacrylamide gels at higher concentrations (%T/%C) than is normally expected or used. Table 8 below gives the ranges of polyacrylamide gel concentrations (%T/%C) and the corresponding ranges of DNA fragments that can be optimally resolved within those gel ranges by this technique. Although some of the low gel concentrations shown in Table 8 have previously been described in the literature for separating macromolecules, eg, 6% DNA sequencing gels, these gel concentrations have not previously been utilized in the manner described herein where molecules have molecular radii larger than the pore size of the gel support (matrix). Table 8 also gives the molecular radius for linear double stranded DNA which approximates the radius of gyration for the larger DNA fragments.

TABLE 8

| OPTIMAL RANGE % T/% C POLYACRYLAMIDE GELS | DNA FRAGMENT LENGTHS (bp) | MOLECULAR RADIUS (nm) |
| --- | --- | --- |
| 40% T/9–12% C to 30% T/8–11% C | 1 to 25 | 0.3–4.2 |
| 35% T/9–12% C to 25% T/6–10% C | 5 to 200 | 1.7–68 |
| 30% T/8–11% C to 20% T/5–9% C | 25 to 1,000 | 4.2–340 |
| 25% T/6–10% C to 15% T4–8% C | 50 to 2,000 | 8.5–680 |
| 20% T/5–9% C to 10% T/3–6% C | 100 to 10,000 | 17–3,400 |
| 15% T/4–8% C to 5% T/2.5–5% C | 200 to >10,000 | 68–>3,400 |
| 10% T/3–6% C to 3% T/2.5–4% C | 500 to >20,000 | 170–>3,400 |

The optimal gel ranges for separating other linear macromolecules can be determined from knowledge of their molecular radius. Also, the approximate pore limit sizes for the various gel compositions can be determined more accurately using standard slab gel procedures and protein molecular weight standards for which the molecular radii are known.

For the gel compositions, micro-gel formats, voltage gradients, and other conditions described above this methodology provides relatively fast separation (1 to 10 minutes) for DNA fragments that range from 10 to 10,000 bp. The methodolgy provides relatively high resolution separations for DNA fragments in the range of 10 to 500 bp and intermediate for DNA fragments in the 500 to 5000 bp range.

Thus, in another embodiment, the present invention contemplates a gel matrix (support) for use in the present microelectrophoresis methods.

A microelectrophoretic gel support medium is therefore contemplated according to the present teachings and based on the discoveries reported herein. The medium has a matrix comprising about 3 to about 40 percent acrylamide and the matrix is about 0.5 to 20.0 millimeters in length along a first axis oriented in the direction of migration of the macromolecules being separated.

To accomodate cooling during electrophoresis to counteract the joule heating that arises during the electrophoretic separation, the medium is about 0.1 to 1.5 millimeters in width perpendicular to said first axis, preferably about 1.0 millimeters in width.

In a preferred embodiment, the gel support is in a cylindrical format, such as in a capillary tube as described herein, preferably a tube having an inner diameter of about 0.25 to about 1.5 millimeters in width, and particularly about 1.0 mm in width.

In an embodiment particularly suited for DNA sequencing of macromolecules of about 2 to about 500 nucleotides in length, a gel matrix in a capillary tube is particularly preferred having an inner diameter of 1.0 mm, an acrylamide concentration of about 15 to about 35 percent acrylamide, and a crosslinker concentration of about 4 to 12 percent bisacrylamide.

The capillary tube can be glass, plastic or any other containment material so long as the ability to detect the migration of the macromolecules in the electrophoretic medium is not obscured.

EXAMPLES

The following examples are given for illustrative purposes only and do not in any way limit the scope of the invention.

1. Separation of PhiX174DNA/Hae III on 12%T/6%C Microgel

Figure 2:
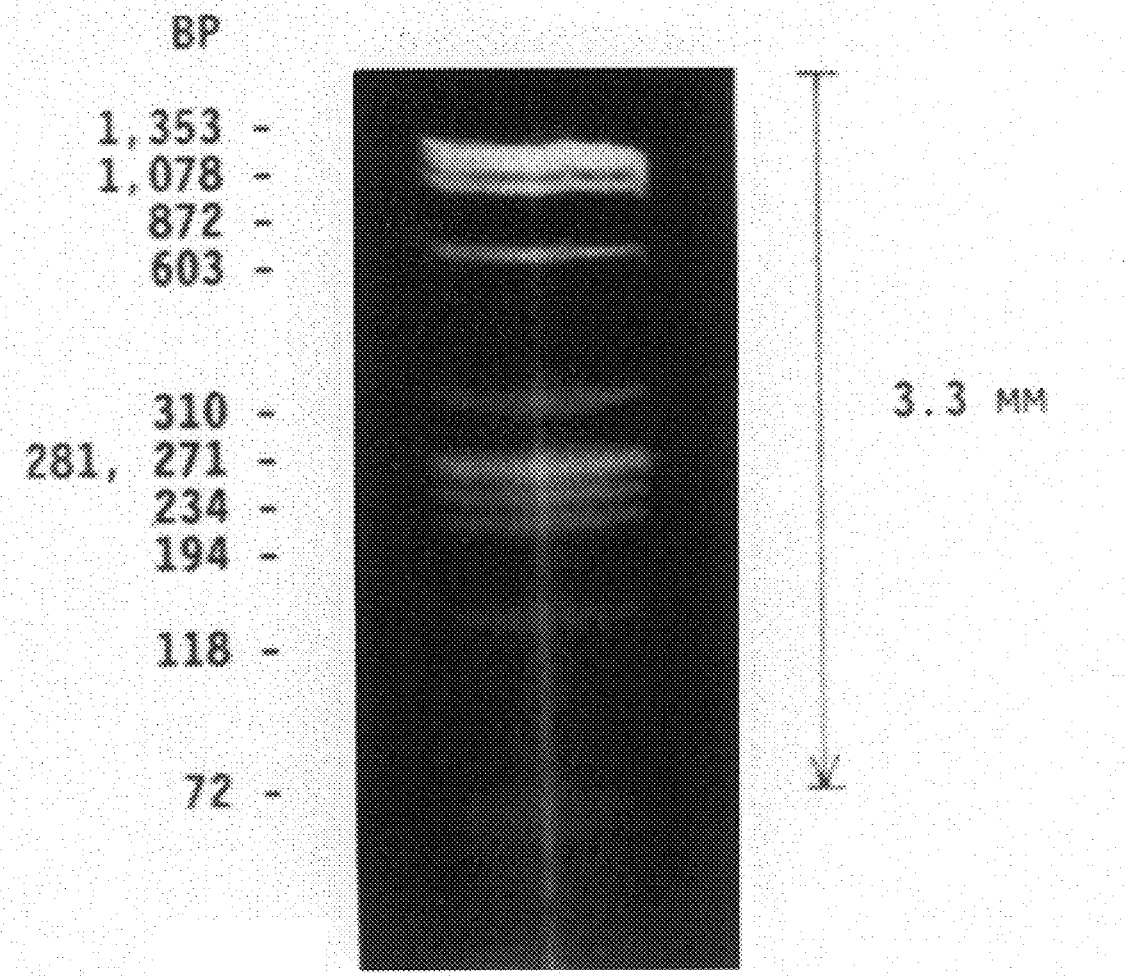
FIG. 2 illustrates a 40X image showing the complete separation of the PhiX174 DNA/Hae III fragment ladder separated on a 6 mm 12%T/6%C micro-gel as described in Example 1. The fragments are separated in a distance of 3.3 mm between the top of the gel and the lowest band.
Figure 3:
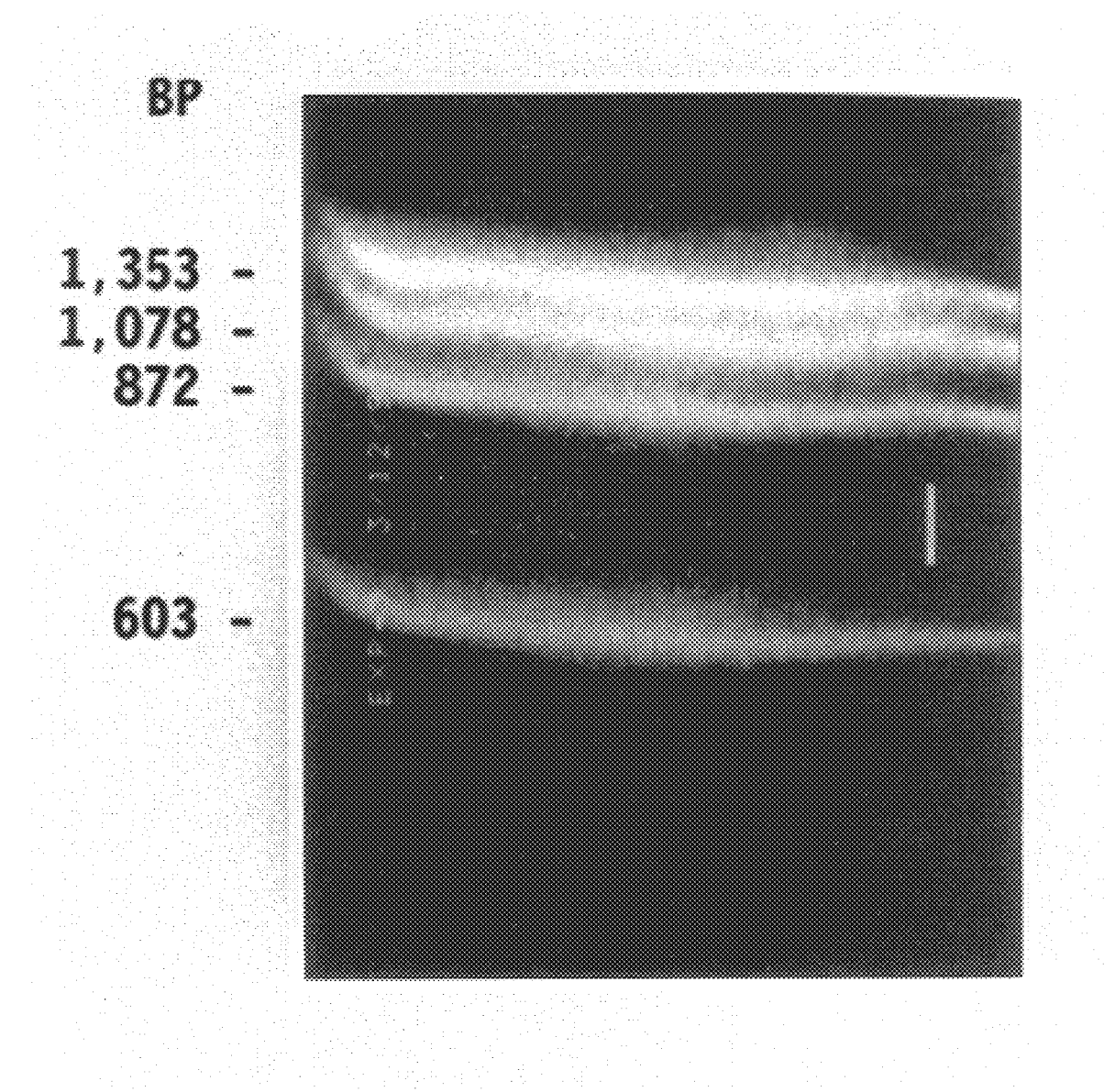
FIG. 3 illustrates a 100X image showing separation of the upper PhiX174 DNA/Hae III restriction fragment ladder carried out on a 6 mm 12%T/6%C micro-gel as described in Example 1. The fragments are separated in a distance of 0.83 mm between the top of the gel and the 603 bp band.
Figure 4:
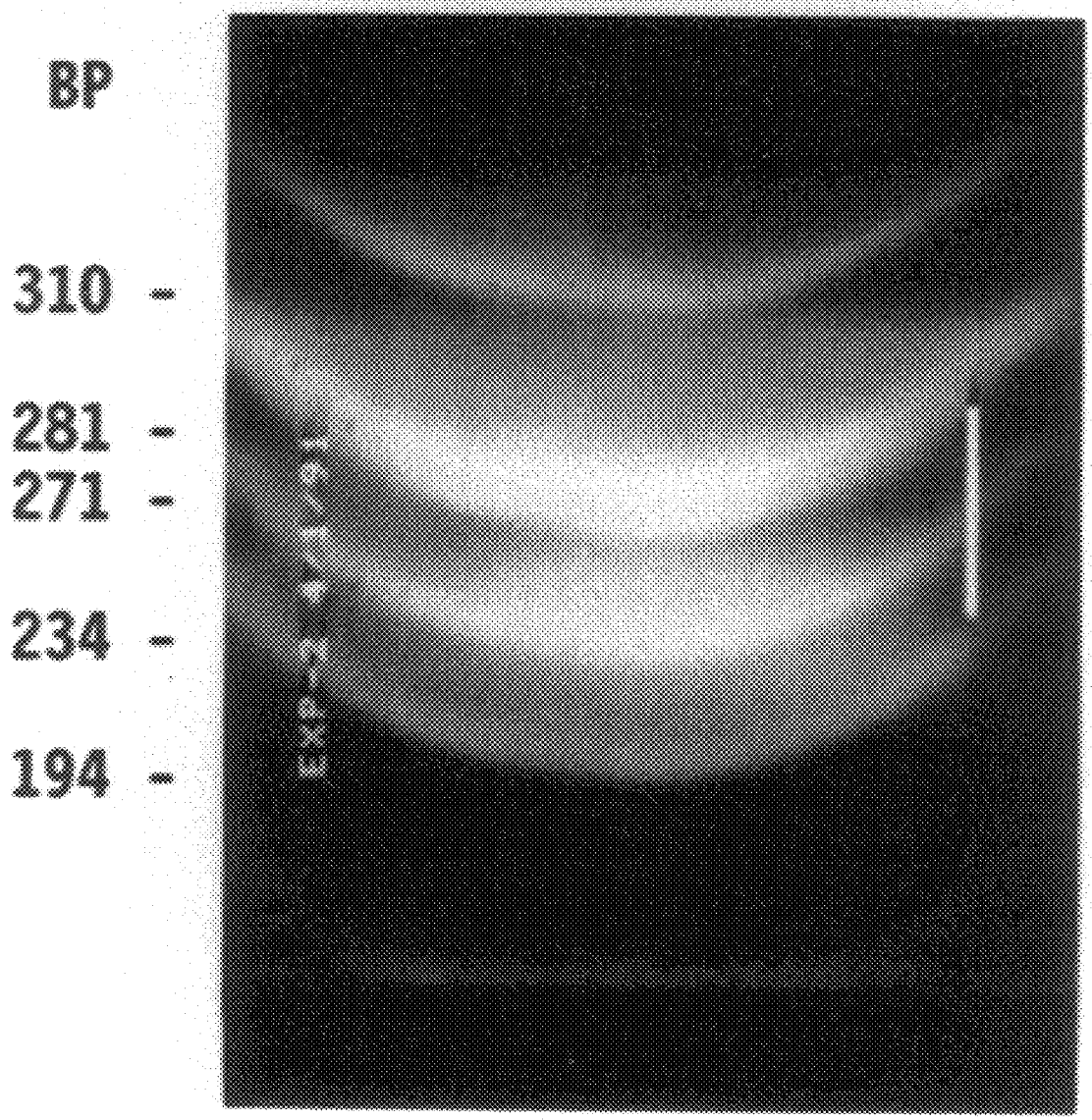
FIG. 4 illustrates a 100X image showing separation of the intermediate PhiX174 DNA/Hae III restriction fragments from the same digest as FIG. 3, showing separation of the 281 bp fragment from the 271 bp fragment. The fragments are separated in a distance of 2.03 mm between the top of the gel and the 194 bp band.

This example demonstrates the separation of the PhiX174DNA/Hae III fragments on a 12%T/6%C microgel. The PhiX174DNA digested with the restriction endonuclease Hae III contains twelve ds-DNA fragments ranging in size from 1,353, 1,078, 872, 603, 310, (281-271), 234, 194, 118, to 72 bp. On most low resolution large scale agarose gels separation of this restriction ladder, resolution of the 281 bp and 271 bp fragments is not observed. For separation by the present invention, a non-denaturing 12%T/6%C micro-gel (6 mm actual gel length) in a 15 mm long (1 mm I.D.) glass capillary was prepared as described herein and used. The micro-gel was first pre-run (electrophoresed) at 33 V/mm for 3 minutes. The running buffer was ½X TBE containing ethidium bromide at a concentration of (250 ng/ml). After pre-running, the micro-gel was flushed with running buffer. Then, approximately 50 nl (0.05 ul) of a sample containing PhiX174DNA/Hae III restriction fragments at a concentration of ($5.7 \times 10^{-14}$ mole/ul) in sample loading buffer (½X TBE, ethidium bromide 500 ng/ml, and 20% glycerol) was added to the top of the micro-gel. (The 50 nl sample applied to the micro-gel contained ~2.8×10$^{-15}$ mole of each DNA fragment). The micro-gel was immediately electrophoresed (22° C.) at 33 V/mm for 2 minutes. The micro-gel was then analyzed and imaged using the epifluorescent microscope imaging system described in the Detection section. Epifluorescent detection for ethidium bromide fluorescence was carried out at an excitation of 450 nm and an emission of 610 nm. The gel was examined and imaged at 40X and 100X magnifications. Images were video recorded, and photographs were later made from the video tapes, using a Sharp GZ-P21 Video Printer. FIG. 2 shows the 40X magnified image of the complete PhiX174DNA/Hae III separation. The vertical bar in FIG. 2 is 0.4 mm to provide an indication of scale. FIG. 3 is a 100X image showing the separation of the upper bands of the restriction ladder. The vertical bar in FIG. 3 is 0.1 mm in height. FIG. 4 is a 100X image showing the separation of the lower bands of the restriction ladder; where separation of the 281 bp and 271 bp bands is observed. Table 9 below gives the separation distances between top of the gel and each band, and the approximate band width for each fragment.

TABLE 9

PhiX174 DNA/Hae III SEPARATION ON 6 mm 12% T/6% C GEL

| Fragment | Size (bp) | Distance (mm) | Band Width (um) |
|---|---|---|---|
| (1) | 1,353 | 0.38 | 36 |
| (2) | 1,075 | 0.46 | 36 |
| (3) | 872 | 0.55 | 36 |
| (4) | 603 | 0.83 | 36 |
| (5) | 310 | 1.48 | 36 |
| (6) | 281 | 1.74 | 48 |
| (7) | 271 | 1.77 | 48 |
| (8) | 234 | 1.91 | 48 |
| (9) | 194 | 2.03 | 48 |
| (10) | 118 | 2.43 | 72 |
| (11) | 72 | 3.29 | 96 |

The results in Example 1 show that the PhiX174 DNA/Hae III fragments were resolved in a distance of ~3.3 mm. The band widths ranged from 36 um to 96 um in thickness.

2. Separation of PHIX174DNA/Hae III on 18%T/6%C Microgel

Figure 5:
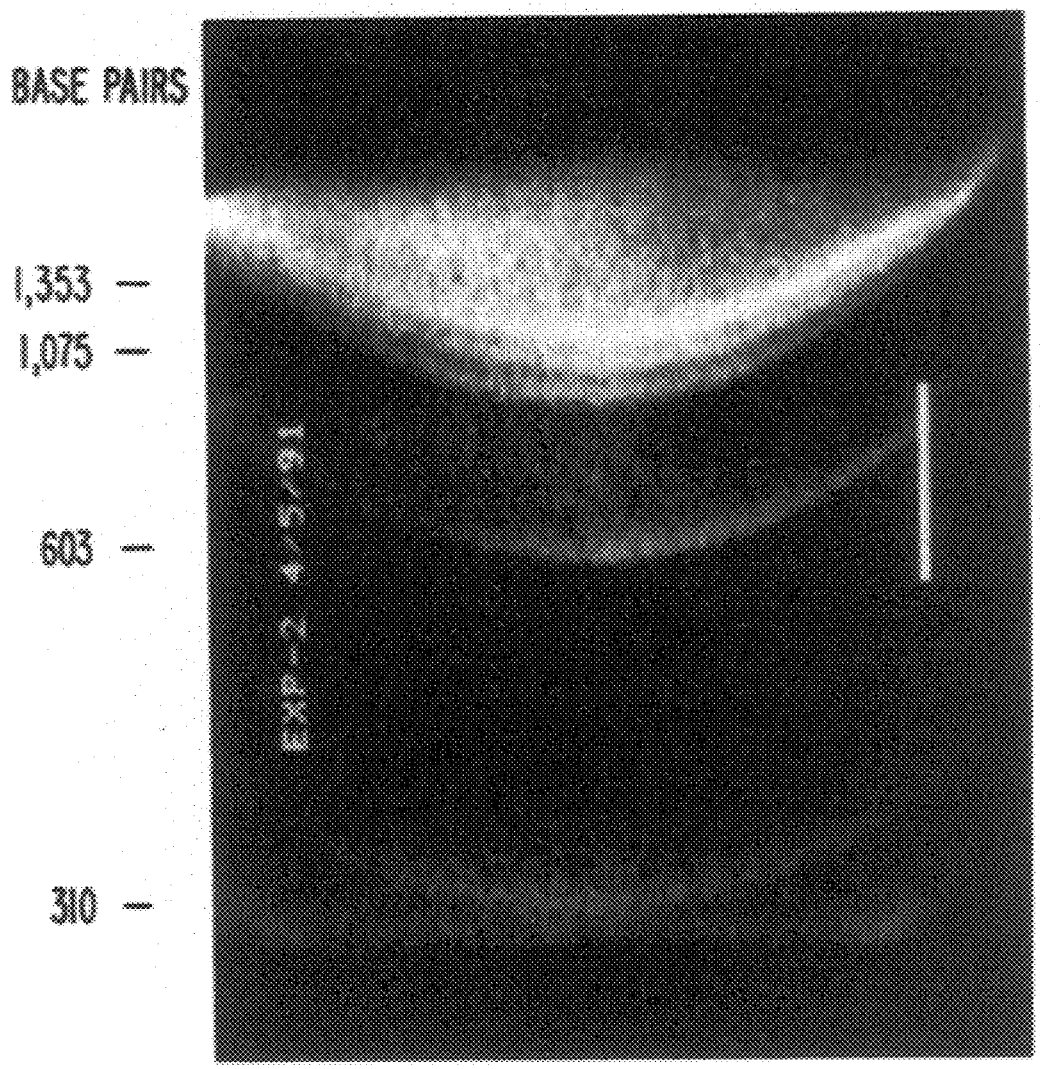
FIG. 5 illustrates a 100X image showing separation of the upper PhiX174 DNA/Hae III restriction fragment ladder bands separated on a 5 mm 18%T/6%C micro-gels described in Example 2. The fragments are separated in a distance of 0.94 mm between the top of the gel and the 310 bp band.

This example demonstrated the separation of the PhiX174DNA/Hae III fragments on a 18%T/6%C micro-gel. For this separation, a non-denaturing 18%T/6%C microgel (5 mm actual gel length) in a 15 mm long (1 mm I.D.) glass capillary was used. The micro-gel was first pre-run (electrophoresed) at 20 V/mm for 3 minutes. The running buffer was ½X TBE containing Ethidium Bromide at a concentration of (250 ng/ml). After pre-running, the micro-gel was flushed with running buffer. Then approximately 20 nl (0.02 ul) of a OX174 DNA/Hae III sample at a concentration of (5.7×10$^{-14}$ mole/ul) in sample loading buffer (½X TBE, ethidium bromide at 500 ng/ml, and 20% glycerol) was added to the top of the micro-gel. (The 20 nl sample applied to the micro-gel contained 1.2×10$^{-15}$ mole of each DNA fragment). The micro-gel was immediately electrophoresed (~22° C.), at 40 V/mm for 1 minute 50 seconds. The micro-gel was then analyzed and imaged using the epifluorescent microscope imaging system described in the Detection section. Epifluorescent detection for ethidium bromide fluorescence was carried out at an excitation of 450 nm and emission of 610 nm. The gel were examined and imaged at 40X and 100X magnifications. Images were video recorded, and photographs were later made from the video tapes, using a Sharp GZ-P21 Video Printer. FIG. 5 shows the 100X magnified image of the upper and some of the intermediate bands. The vertical bar in FIG. 5 is 0.23 mm in height to provide an indication of migration distances. Table 10 below gives the separation distances between top of the gel and each band, and the approximate band width for each fragment.

TABLE 10

PhiX174 DNA/Hae III SEPARATION ON 5 mm 18% T/6% C GEL

| Fragment | Size (bp) | Distance (mm) | Band Width (um) |
|---|---|---|---|
| (1) | 1,353 | 0.29 | 18 |
| (2) | 1,075 | 0.32 | 18 |
| (3) | 872 | 0.35 | 18 |
| (4) | 603 | 0.54 | 24 |
| (5) | 310 | 0.94 | 24 |
| (6) | 281 | 1.08 | 36 |
| (7) | 271 | 1.10 | 36 |
| (8) | 234 | 1.17 | 36 |
| (9) | 194 | 1.25 | 36 |
| (10) | 118 | 1.39 | 48 |
| (11) | 72 | 1.70 | 60 |

The results in Example 2 show that the PhiX174 DNA/Hae III fragments were resolved in a distance of only ~1.7 mm. The band widths ranged from 18 um to 60 um in thickness.

3. Separation of PhiX174DNA/Hae III on 26%T/6%C Microgel

This example demonstrated the separation of the PhiX174DNA/Hae III fragments on a 26%T/6%C micro-gel. The PhiX174DNA/Hae III contains twelve ds-DNA fragments ranging in size from 1,353, 1,078, 872, 603, 310, (281-271), 234, 194, 118, to 72 bp. For this separation, a non-denaturing 26%T/6%C micro-gel (5 mm actual gel length) in a 15 mm long (1 mm I.D.) glass capillary was used. The micro-gel was first pre-run (electrophoresed) at 40 V/mm for 2 minutes. The running buffer was ½X TBE containing Ethidium Bromide at a concentration of (250 ng/ml). After the pre-running, the micro-gel was flushed with running buffer. Then, approximately 20 nl (0.02 ul) of a PhiX174 DNA/Hae III sample at a concentration of (5.7×10$^{-14}$ mole/ul) in sample loading buffer (½X TBE, ethidium bromide 500 ng/ml, and 20% glycerol) was added to the top of the micro-gel. (The 20 nl sample applied to the micro-gel contained 1.2×10$^{-15}$ mole of each DNA fragment). The micro-gel was immediately electrophoresed (~22° C.), at 40 V/mm for 2 minutes 55 seconds. The micro-gel was then analyzed and imaged using the epifluorescent microscope imaging system described in the Detection section. Epifluorescent detection for ethidium bromide fluorescence was carried out at an excitation of 450 nm and an emission of 610 nm. The gels were examined and imaged at 40X and 100X magnifications. Images were video recorded. Results showed that except for the upper two bands (1,353 bp and 1,075 bp) the PhiX174 DNA/Hae III fragments were resolved in a running distance of less than 1.5 mm.

4. Separation of Fluorescent 18-mer, 21-mer, 23-mer, and 32-mer Oligonucleotides on a 26%T/6%C Microgel This example demonstrates the separation of a mixture of fluorescent 18-mer, 21-mer, 23-mer, and 32-mer oligonucleotides (single stranded) on a 26%T/6%C micro-gel. Each of the oligonucleotides was labelled at its 5'-terminal position with fluorescein. For this separation, a denaturing 26%T/6%C micro-gel containing 6M Urea 1X TBE buffer was used. The micro-gel was a 20 mm long (1 mm I.D.) glass capillary containing a 13 mm long gel. The micro-gel was first pre-run (electrophoresed) at 20 V/mm (200 V/cm) for 1 minute. The running buffer used was ½X TBE. After the pre-running, the micro-gel was flushed with running buffer.

Figure 6:
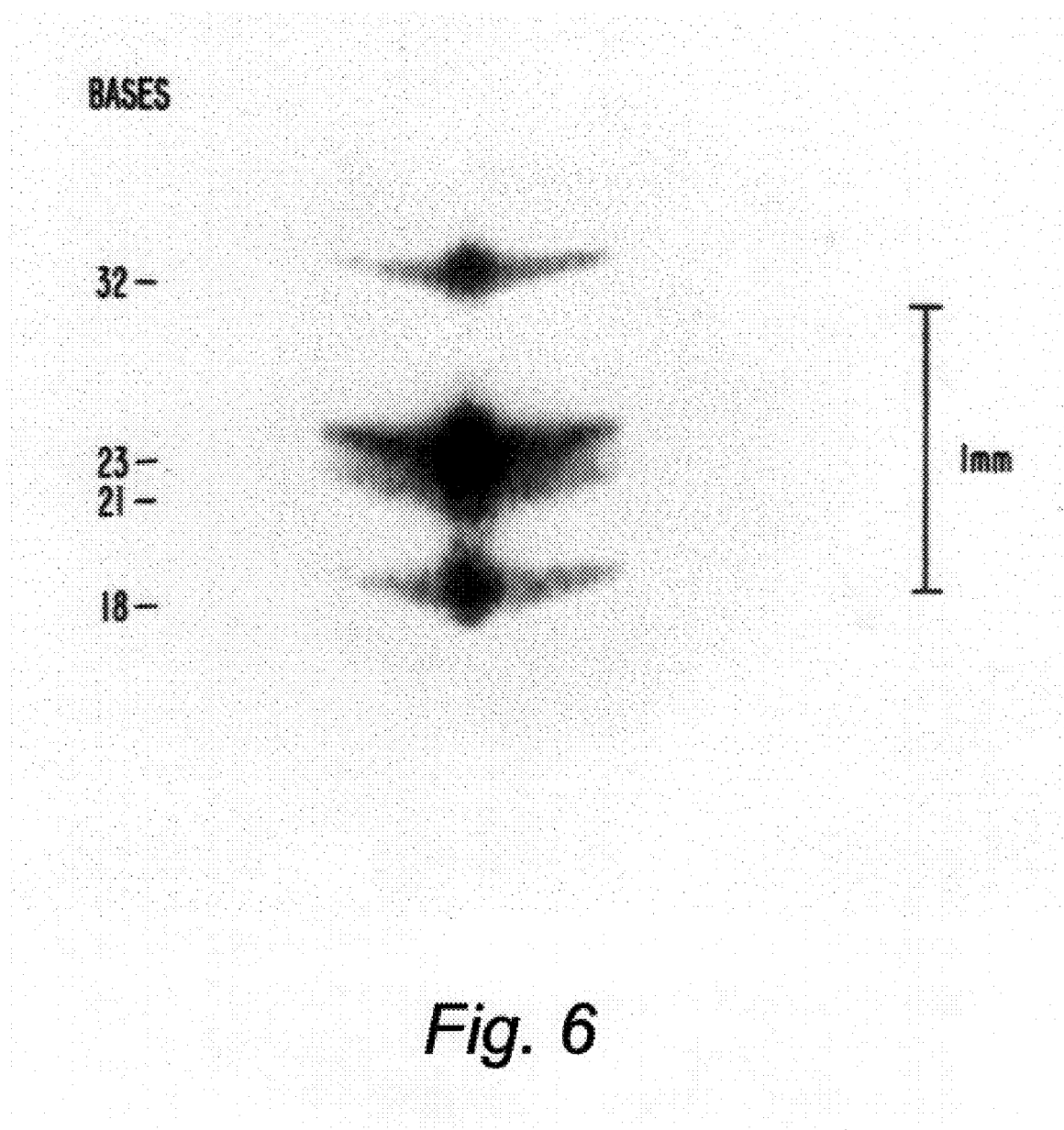

Approximately 50 nl (0.05 ul) of the fluorescent oligonucleotide mixture at a concentration of [5.0×10$^{-13}$ mole(each oligo)/ul] in sample loading buffer (½X TBE, and 30% glycerol) was added to the top of the micro-gel. (The 50 nl sample applied to the micro-gel contains 2.5×10$^{-14}$ mole of each fluorescent oligonucleotide). The micro-gel was immediately electrophoresed, at room temperature (~22 C) at 15 V/mm for 6 minutes. The micro-gel was then analyzed and imaged using the epifluorescent microscope imaging system described in the Detection section. Epifluorescent detection for fluorescein fluorescence was carried out at an excitation 450 nm and emission of 520 nm. The gels were examined and imaged at 40X and 100X magnifications. Images were video recorded. FIG. 6 shows the 40X image results. The results show the resolution of all the fragments, including the 21-mer and 23-mer. The measured distance between the top of the gel and the lowest band (i.e., separation length) was measured to be 4.6 mm. This 2 base resolution was obtained in a total running distance of less than 5 mm. The band width of the 32-mer is <100 um (0.1 mm). These results indicate that a 100 base per centimeter resolution is produced for DNA fragments in the 10 bp to 100 bp range using the above-described gel system.

The foregoing description and the examples are intended as illustrative and are not to be taken as limiting. Still other variations within the spirit and scope of this invention are possible and will readily present themselves to those skilled in the art. Other embodiments are within the following claims.

What is claimed is:

1. An electrophoretic system for the analysis of multiple biological samples in an array format comprising:
   a sheet of material,
   an array of 10 or more lanes of gel supported on the sheet of material, each lane having a length and a width, the width defined by that portion of the gel which the sample first contacts, the width of each lane being 1 mm or less, the lanes being separated from one another, and the length of the lanes being 25 mm or less,
   a power supply operatively connected to the system to provide electrophoretic motion of the biological samples, and
   an electronic imaging apparatus, the apparatus being positioned to simultaneously image the entire array.

2. The electrophoretic system of claim 1 wherein the sheet of material is a glass sheet.

3. The electrophoretic system of claim 1 wherein the sheet of the material is a microchannel plate.

4. The electrophoretic system of claim 1 wherein the imaging apparatus is a charge coupled device (CCD).

5. The electrophoretic system of claim 1 wherein the imaging apparatus is an intensified charge coupled device.

6. The electrophoretic system of claim 1 wherein the imaging apparatus is a cooled charge coupled device.

7. The electrophoretic system of claim 1 wherein the imaging apparatus is a silicon intensified tube.

8. The electrophoretic system of claim 1 wherein the lanes are separated by plastic spacer material.

9. The electrophoretic system of claim 1 wherein the lanes are separated by glass spacer material.

10. The electrophoretic system of claim 1 wherein the sheet is a microchanneled sheet.

11. The electrophoretic system of claim 1 wherein the sheet is a microchanneled glass sheet.

12. The electrophoretic system of claim 1 wherein the length of the lanes is 10 mm or less.

13. The electrophoretic system of claim 1 wherein the width of the lane is less than 0.1 mm.

14. The electrophoretic system of claim 1 wherein the imaging apparatus is combined with a microscope.

15. The electrophoretic system of claim 14 wherein the magnification is at least 40X.

16. The electrophoretic system of claim 14 wherein the magnification is at least 100X.

17. The electrophoretic system of claim 14 wherein the microscope includes a filter for filtering excitation radiation and emitted radiation.

18. The electrophoretic system of claim 1 wherein the imaging apparatus is a real-time imaging apparatus.

19. The electrophoretic system of claim 1 further including a source of excitation radiation.

20. The electrophoretic system of claim 1 wherein the biological sample includes nucleic acid fragments which range in size from 2 nucleotides to substantially 1000 nucleotides and the gel is a restrictive pore media with pore limit diameters between substantially 2.0 nanometers and 5.0 nanometers.

21. The electrophoretic system of claim 1 wherein the biological sample includes nucleic acid fragments which range in size from substantially 10 nucleotides to substantially 2,000 nucleotides and the gel is a restrictive pore media with pore limit diameters between 2.0 nanometers and 6.7 nanometers.

22. The electrophoretic system of claim 1 wherein the gel is formed of a total of about 12–40% of polyacrylamide with 4 to 12% cross-linking agent to form a cross-linked polyacrylamide gel.

23. The electrophoretic system of claim 1 wherein the gel is formed of a total of about 15–35% of polyacrylamide with 4 to 12% cross-linking agent to form a cross-linked polyacrylamide gel.

24. The electrophoretic system of claim 1 wherein the gel is formed to be about 0.25 to 1.0 millimeters thick.

25. The electrophoretic system of claim 1 wherein the imaging system determines the relative location of the various biological samples within the sample.

26. The electrophoretic system of claim 1 wherein the imaging apparatus comprises a photon counting device.

27. The electrophoretic system of claim 1 wherein the sheet is silicon.

28. The electrophoretic system of claim 1 wherein the gel is agarose.

29. The electrophoretic system of claim 1 wherein the gel comprises starch.

30. The electrophoretic system of claim 1 wherein the gel comprises hydrogel.

31. An electrophoretic system for the analysis of multiple biological samples in an array format comprising:
   a parallel array of 10 or more capillary tubes, each capillary tube having an internal diameter of 1 mm or less, the capillary tubes having a length of 25 mm or less;
   a gel disposed in at least a portion of each of the capillary tubes;
   a power supply operatively connected to the system to provide electrophoretic motion of the biological samples; and
   an electronic imaging apparatus, the apparatus being positioned to simultaneously image the entire array.

32. An electrophoretic system of claim 31, the electronic imaging apparatus further comprising a microscope.

33. An electrophoretic system of claim 31, wherein the parallel array of capillary tubes are vertically oriented.

34. An electrophoretic system of claim 31, further comprising a micromanipulator having a syringe for the delivery of samples to the parallel array of capillary tubes.

35. An electrophoretic system of claim 31, wherein a portion of each capillary tube is used to receive a sample.

* * * * *